United States Patent
Oostman, Jr.

(10) Patent No.: US 9,877,745 B2
(45) Date of Patent: *Jan. 30, 2018

(54) SYSTEMS AND METHODS FOR HARVESTING, STORING, AND IMPLANTING HAIR GRAFTS

(71) Applicant: Restoration Robotics, Inc., San Jose, CA (US)

(72) Inventor: Clifford A. Oostman, Jr., Hansville, WA (US)

(73) Assignee: RESTORATION ROBOTICS, INC., San Jose, CA (US)

( * ) Notice: Subject to any disclaimer, the term of this patent is extended or adjusted under 35 U.S.C. 154(b) by 418 days.

This patent is subject to a terminal disclaimer.

(21) Appl. No.: 14/572,653

(22) Filed: Dec. 16, 2014

(65) Prior Publication Data

US 2015/0133962 A1     May 14, 2015

Related U.S. Application Data

(63) Continuation of application No. 13/541,527, filed on Jul. 3, 2012, now Pat. No. 8,951,267, which is a
(Continued)

(51) Int. Cl.
*A61B 17/34* (2006.01)
*A61B 17/00* (2006.01)
(Continued)

(52) U.S. Cl.
CPC .......... *A61B 17/3468* (2013.01); *A61B 17/00* (2013.01); *A61B 34/30* (2016.02);
(Continued)

(58) Field of Classification Search
CPC ....... A61F 2/10; A61B 17/3468; A61B 17/00; A61B 34/30; A61B 34/37; A61B 2034/305; A61B 2010/0225; A61B 2017/00752
See application file for complete search history.

(56) References Cited

U.S. PATENT DOCUMENTS

| | | |
|---|---|---|
| 2,366,886 A | 1/1945 | Tuyl |
| 4,154,239 A | 5/1979 | Turley |

(Continued)

FOREIGN PATENT DOCUMENTS

| | | |
|---|---|---|
| JP | 2002177283 | 6/2002 |
| WO | WO 1995/028896 | 11/1995 |

(Continued)

OTHER PUBLICATIONS

Extended European Search and European Search Opinion dated Feb. 22, 2017, in connection with commonly assigned European Patent Application No. 16200790.0, (5 pages).

(Continued)

*Primary Examiner* — Ashley Fishback

(57) ABSTRACT

A system and method for harvesting, storing, and implanting biological units, in particular hair follicular units (FUs). The system is particularly useful to facilitate hair transplant procedures. The system may comprise an implanting tool, a cartridge with a plurality of receptacles for biological units and one or more control mechanisms. The device and cartridge for storing biological units may be incorporated within an overall automated or robotic system, or may form part of a semi-automated or even manual apparatus.

20 Claims, 16 Drawing Sheets

Related U.S. Application Data continuation of application No. 12/196,524, filed on Aug. 22, 2008, now Pat. No. 8,882,783, which is a continuation of application No. 12/194,370, filed on Aug. 19, 2008, now Pat. No. 8,211,134.

(60) Provisional application No. 60/997,188, filed on Sep. 29, 2007.

(51) Int. Cl.
*A61F 2/10* (2006.01)
*A61B 34/30* (2016.01)
*A61B 34/37* (2016.01)
*A61B 10/02* (2006.01)

(52) U.S. Cl.
CPC ............... *A61B 34/37* (2016.02); *A61F 2/10* (2013.01); *A61B 2010/0225* (2013.01); *A61B 2017/00752* (2013.01); *A61B 2034/305* (2016.02)

(56) References Cited

U.S. PATENT DOCUMENTS

| | | | |
|---|---|---|---|
| 4,451,254 | A | 5/1984 | Dinius et al. |
| 4,485,933 | A | 12/1984 | Sykes |
| 5,417,683 | A | 5/1995 | Shiao |
| 5,439,475 | A | 8/1995 | Bennett |
| 5,584,851 | A | 12/1996 | Banuchi |
| 5,611,811 | A | 3/1997 | Goldberg |
| 5,643,308 | A | 7/1997 | Markman |
| 5,653,688 | A | 8/1997 | Mills et al. |
| 5,782,843 | A | 7/1998 | Aasberg |
| 5,782,851 | A | 7/1998 | Rassman |
| 5,792,169 | A | 8/1998 | Markman |
| 5,817,120 | A | 10/1998 | Rassman |
| 5,827,297 | A | 10/1998 | Boudjema |
| 5,868,758 | A | 2/1999 | Markman |
| 5,873,888 | A | 2/1999 | Costanzo |
| 5,895,403 | A | 4/1999 | Collinsworth |
| 5,951,572 | A | 9/1999 | Markman |
| 6,027,512 | A | 2/2000 | Bridges |
| 6,056,736 | A | 5/2000 | Markman |
| 6,059,807 | A | 5/2000 | Boudjema |
| 6,270,511 | B1 | 8/2001 | Markman |
| 6,572,625 | B1 | 6/2003 | Rassman |
| 6,585,746 | B2 | 7/2003 | Gildenberg |
| 6,973,931 | B1 | 12/2005 | King |
| 7,144,406 | B2 | 12/2006 | Pak et al. |
| 7,477,782 | B2 | 1/2009 | Qureshi et al. |
| 7,481,820 | B1 | 1/2009 | Keene |
| 7,627,157 | B2 | 12/2009 | Qureshi et al. |
| 2002/0103222 | A1 | 8/2002 | Mangat |
| 2002/0103500 | A1 | 8/2002 | Gildenberg |
| 2003/0040766 | A1 | 2/2003 | Werner |
| 2003/0087454 | A1 | 5/2003 | Schultz et al. |
| 2004/0116942 | A1 | 6/2004 | Feller |
| 2004/0220589 | A1 | 11/2004 | Feller |
| 2005/0272972 | A1 | 12/2005 | Iddan |
| 2006/0127881 | A1 | 6/2006 | Wong et al. |
| 2006/0195047 | A1 | 8/2006 | Freeman et al. |
| 2007/0078466 | A1 | 4/2007 | Bodduluri et al. |
| 2007/0106307 | A1 | 5/2007 | Bodduluri |
| 2007/0287984 | A1 | 12/2007 | Lobl |
| 2008/0033455 | A1 | 2/2008 | Rassman et al. |
| 2008/0050805 | A1 | 2/2008 | Cole et al. |
| 2009/0052738 | A1 | 2/2009 | Qureshi et al. |

FOREIGN PATENT DOCUMENTS

| | | |
|---|---|---|
| WO | WO 2001/064111 | 9/2001 |
| WO | WO 2005/009491 | 2/2005 |
| WO | WO 2005/074820 | 8/2005 |
| WO | WO 2007/021904 | 2/2007 |
| WO | WO 2007/041267 | 4/2007 |
| WO | WO 2008/024954 | 2/2008 |
| WO | WO 2008/024955 | 2/2008 |

OTHER PUBLICATIONS

Office Action mailed on connection with commonly assigned Canadian Patent Application No. 2,790,776, dated Mar. 13, 2015, (4 pages).
Amendment and Response to Oct. 7, 2010 Office Action in relation to U.S. Appl. No. 12/196,524, 11 pages.
Communication from Australian Patent Office, dated Apr. 1, 2011, in relation to commonly assigned Australian Patent Application No. 12008307698, which is an Australian National Stage filing of PCT/US2008/010024, 4 pages.
Communication from Canadian Patent Office, dated Jan. 30, 2013, in relation to commonly assigned Canadian Patent Application No. 2,696,201, which is the Canadian National Stage filing of PCT/US2008/010034. 2 pages.
Communication from Chinese Patent Office, dated May 31, 2011 (in Chinese and an English Translation), in relation to commonly assigned Chinese Patent Application No. 200880107304.0, which is a Chinese National Stage filing of PCT/US2008/010034, 9 pages.
Communication from Chinese Patent Office, dated Nov. 22, 2012 (an English Translation thereof), in relation to commonly assigned Chinese Patent Application No. 200880107304.0, which is a Chinese National Stage filing of PCT/US2008/010034, 2 pages.
Communication from Japanese Patent Office, dated Sep. 3, 3013 (an English Translation thereof in relation to commonly assigned Japanese Patent Application No. 2012/144376, Sep. 3, 2013, (3 pages).
Communication from Japanese Patent Office, dated Apr. 3, 2012 (an English Translation thereof), in relation to commonly assigned Japanese Patent Application No. 2010-526889, which is a Japanese National Stage filing of PCT/US2008/010034, 3 pages.
Final Office Action dated Mar. 10, 2011, in connection with U.S. Appl. No. 12/196,524, 13 pages.
Interview Summary dated Jun. 21, 2010, in relation to U.S. Appl. No. 12/196,524, Applicant Restoration Robotics, Inc., 4 pages.
Non-Final Office Action dated Apr. 13, 2010, in relation to U.S. Appl. No. 12/196,524, Applicant Restoration Robotics, Inc., 14 pages.
Non-Final Office Action dated Mar. 3, 2011, in relation to U.S. Appl. No. 12/194,370, 14 pages.
Office Action dated Oct. 11, 2013, in relation to commonly assigned Canadian Patent Application No. 2,790,776, (3 pages).
Office Action dated Dec. 23, 2011, in relation to commonly assigned Australian Patent Application No. 2008307698, (2 pages), 2 pages.
Office Action dated Dec. 27, 2012 in relation to commonly assigned Canadian Patent Application No. 2,790,776, Dec. 27, 2012, 3 pages.
Office Action dated Jul. 11, 2014 in connection with comonly assigned Canadian Patent Application No. 2,790,776, (3 pages).
Office Action dated Nov. 9, 2011, in relation to commonly assigned U.S. Appl. No. 12/194,370, 15 pages.
Office Action dated Oct. 6, 2011, in relation to commonly assigned Korean Patent Application No. 10-2010-7005772, in Korean and with English Translation (8 pages), 8 pages.
Office Action dated Oct. 7, 2010 in connection with U.S. Appl. No. 12/196,524, 12 pages.
Office Action dated Sep. 6, 2011, in relation to commonly assigned U.S. Appl. No. 12/348,811 (14 pages), 14 pages.
PCT International Search Report and Written Opinion of PCT/US2008/010034, Applicant Restoration Robotics, Inc., Forms PCT/ISA/210, 220 and 237, dated Feb. 4, 2009, 16 pages.
PCT International Search Report and Written Opinion of PCT/US2009/030326 Applicant Restoration Robotics, Inc. Forms PCT/ISA/210,220 and 237, dated May 14, 2009, 15 pages.
PCT Invitation to Pay Additional Fees of PCT/US2008/010034, Applicant Restoration Robotics, Inc. Form PCT/ISA/206, dated Oct. 23, 2008, 4 pages.
Response to Final Office Action dated Mar. 10, 2011, in connection with U.S. Appl. No. 12/196,524, 12 pages.

(56) References Cited

OTHER PUBLICATIONS

Response to Office Action dated Jun. 14, 2010, in relation to U.S. Appl. No. 12/196,524, Applicant Restoration Robotics, Inc., 9 pages.
Bernstein, et al., "The Logic of Follicular Unit Transplantation", Dermatologic Clinics vol. 17, No. 2, Apr. 1999, 277-296.
Lee, et al., "New Instrument for Hair Transplant: Multichannel Hair Transplanter", Dermatol Surg 2005. 31:379, 2005, 1 page.
Rassman, et al., "Rapid Fire Hair Implanter Carousel", From New Hair Institute—Internet. (Dermatologic Surgery, vol. 24, 1998—pp. 623-627), Feb. 16, 2006, 7 pages.
English Translation of Japanese Office Action dated Jun. 2, 2015, in connections to commonly assigned Japanese Patent Application No. 2014-139433, (5 pages).

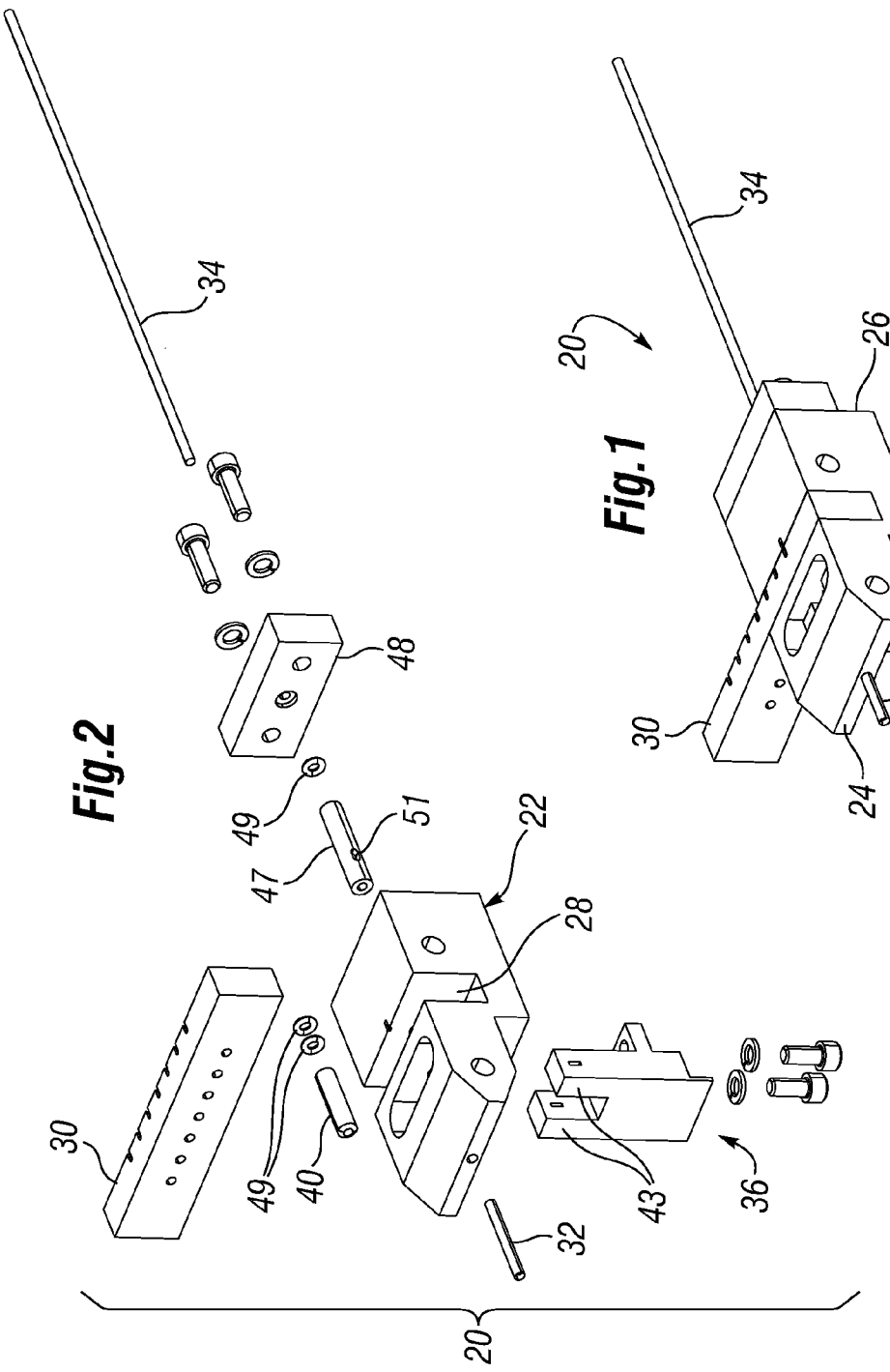

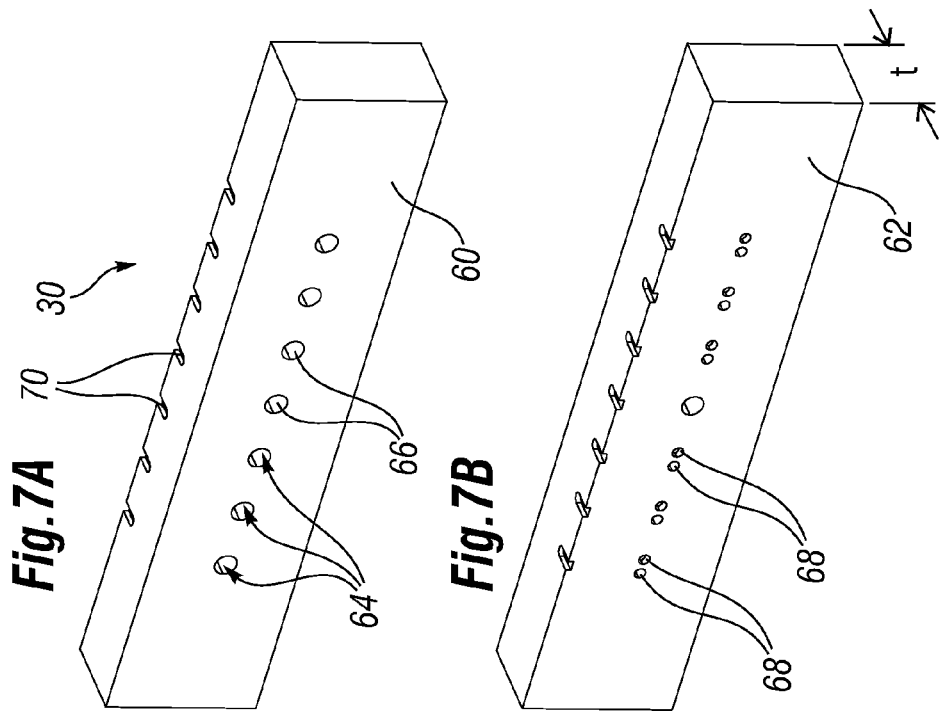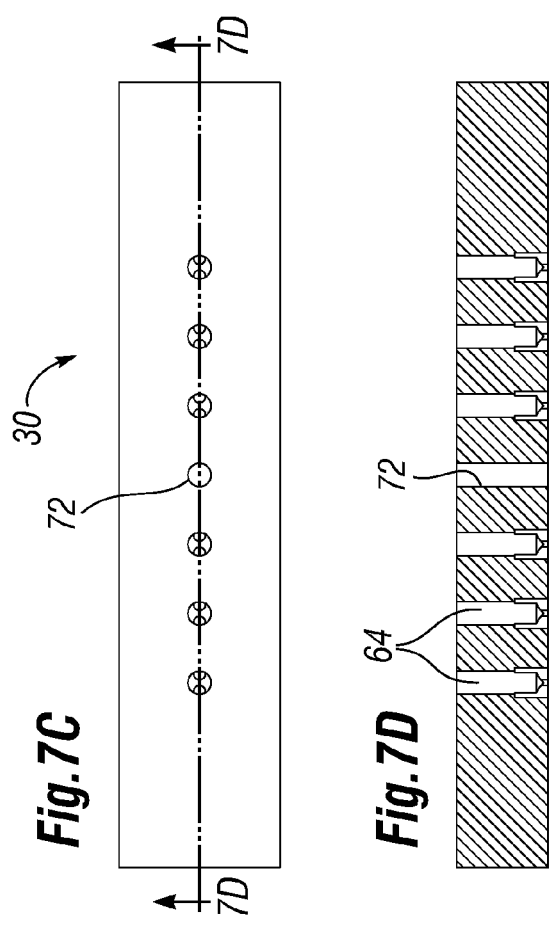

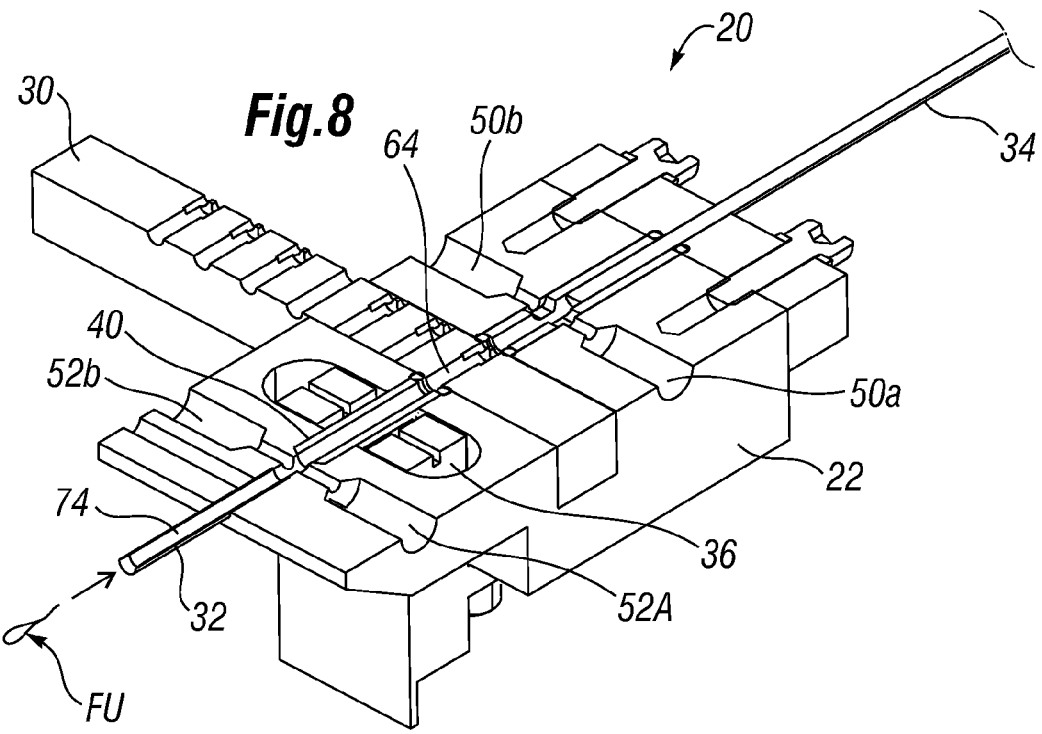
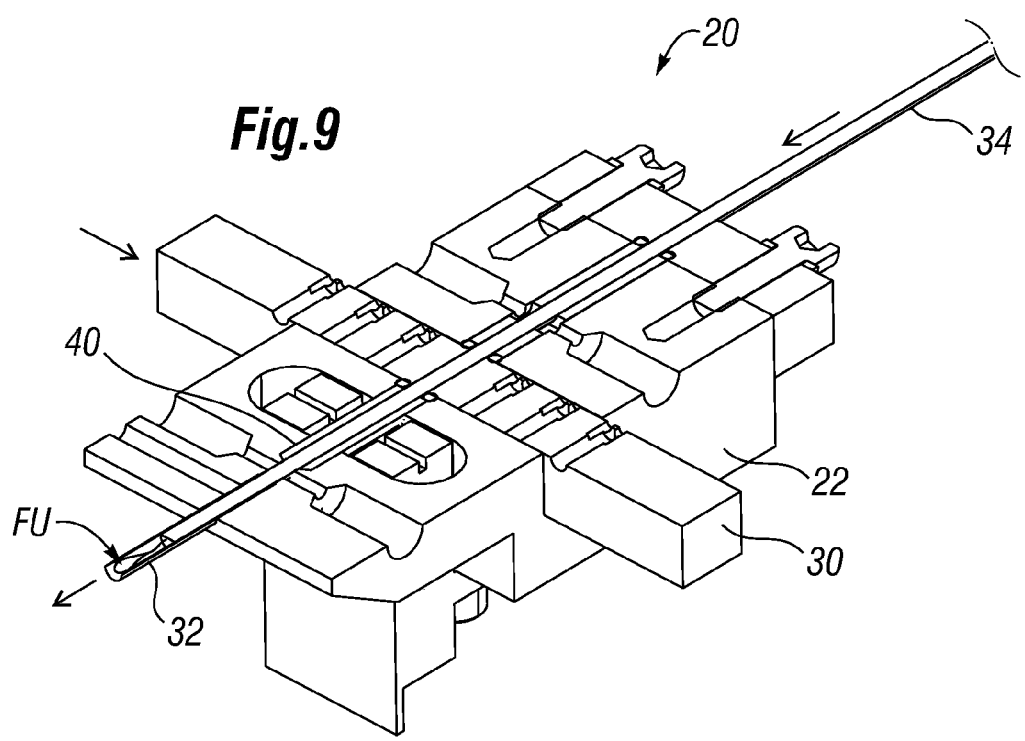

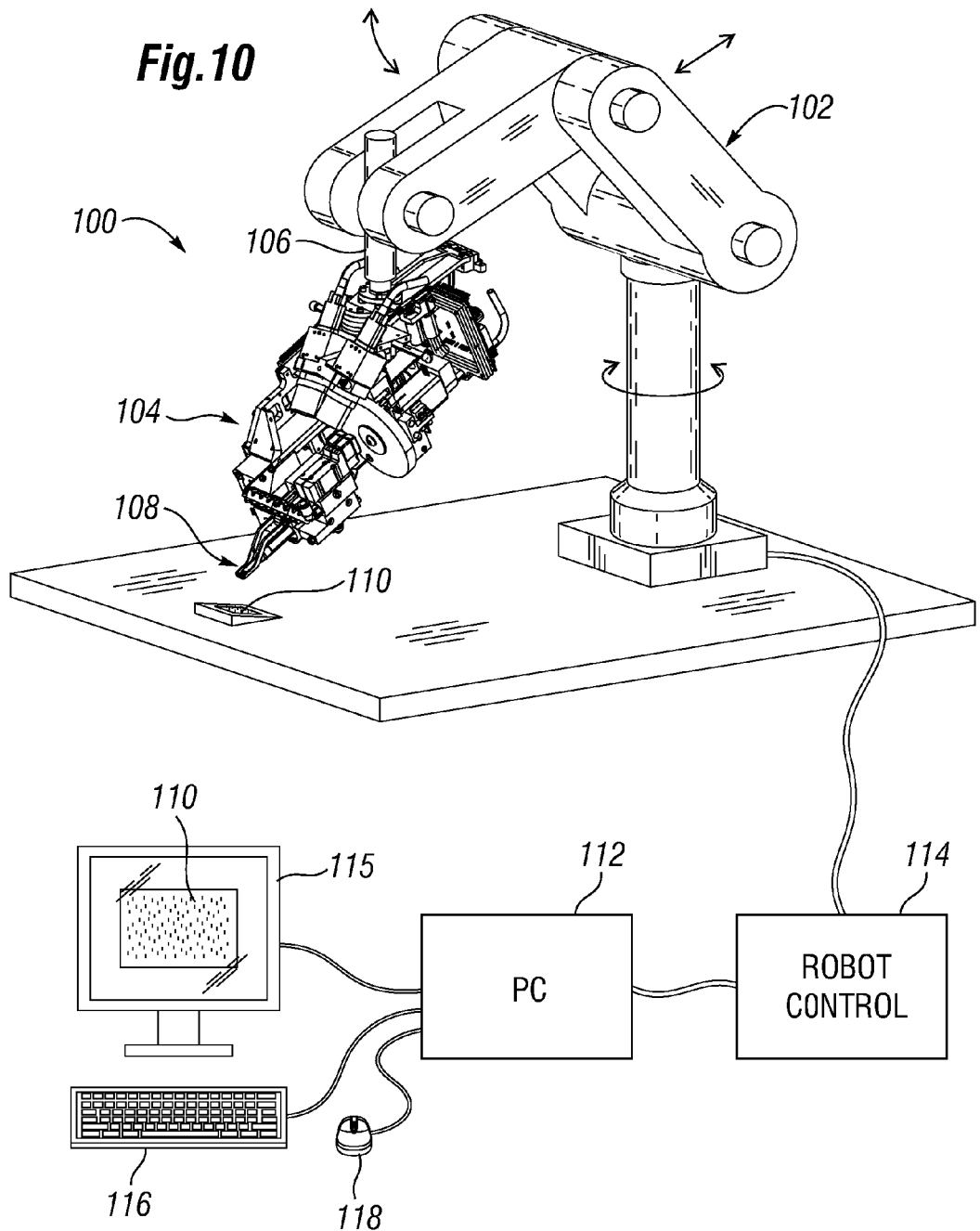

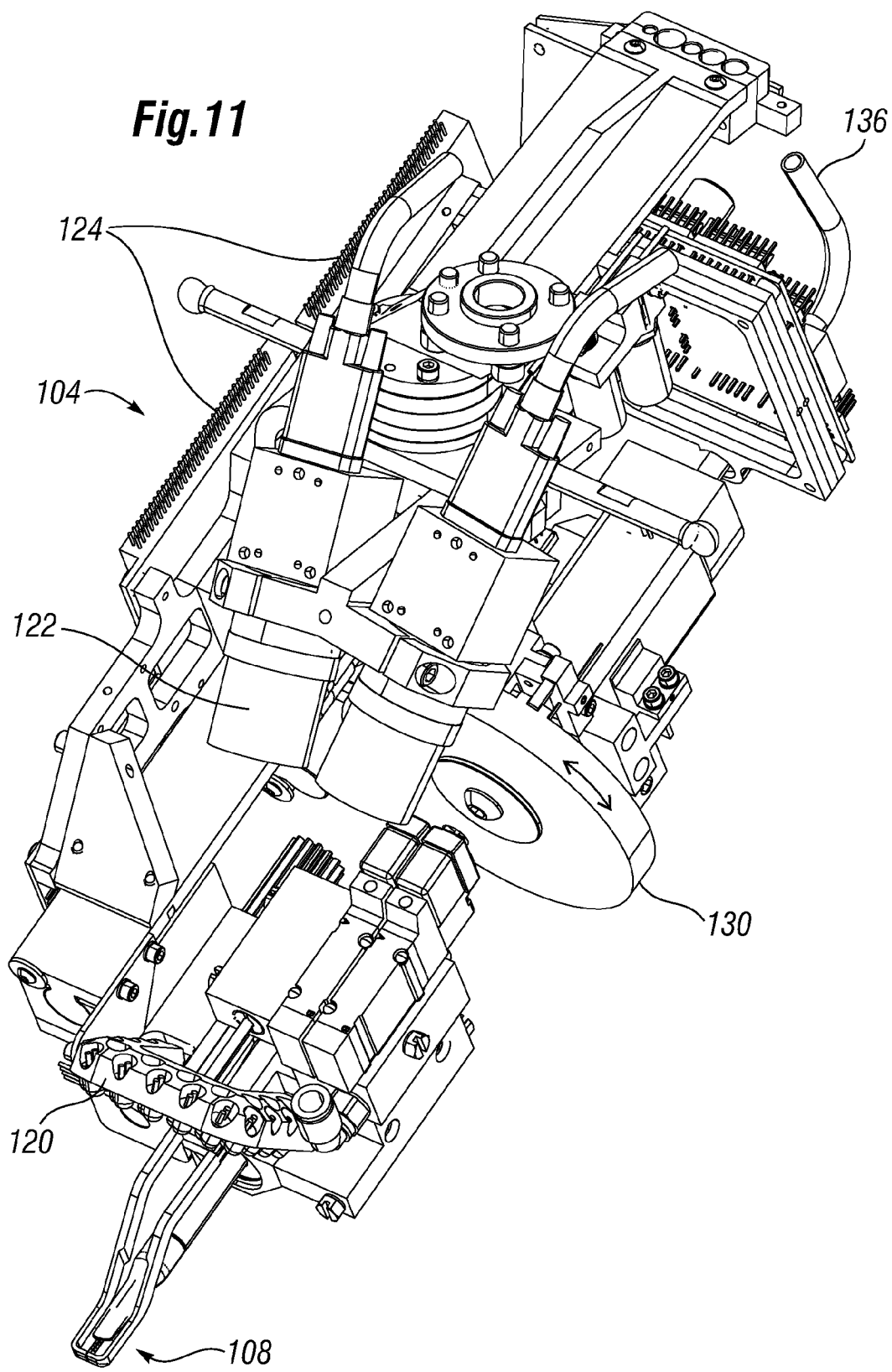

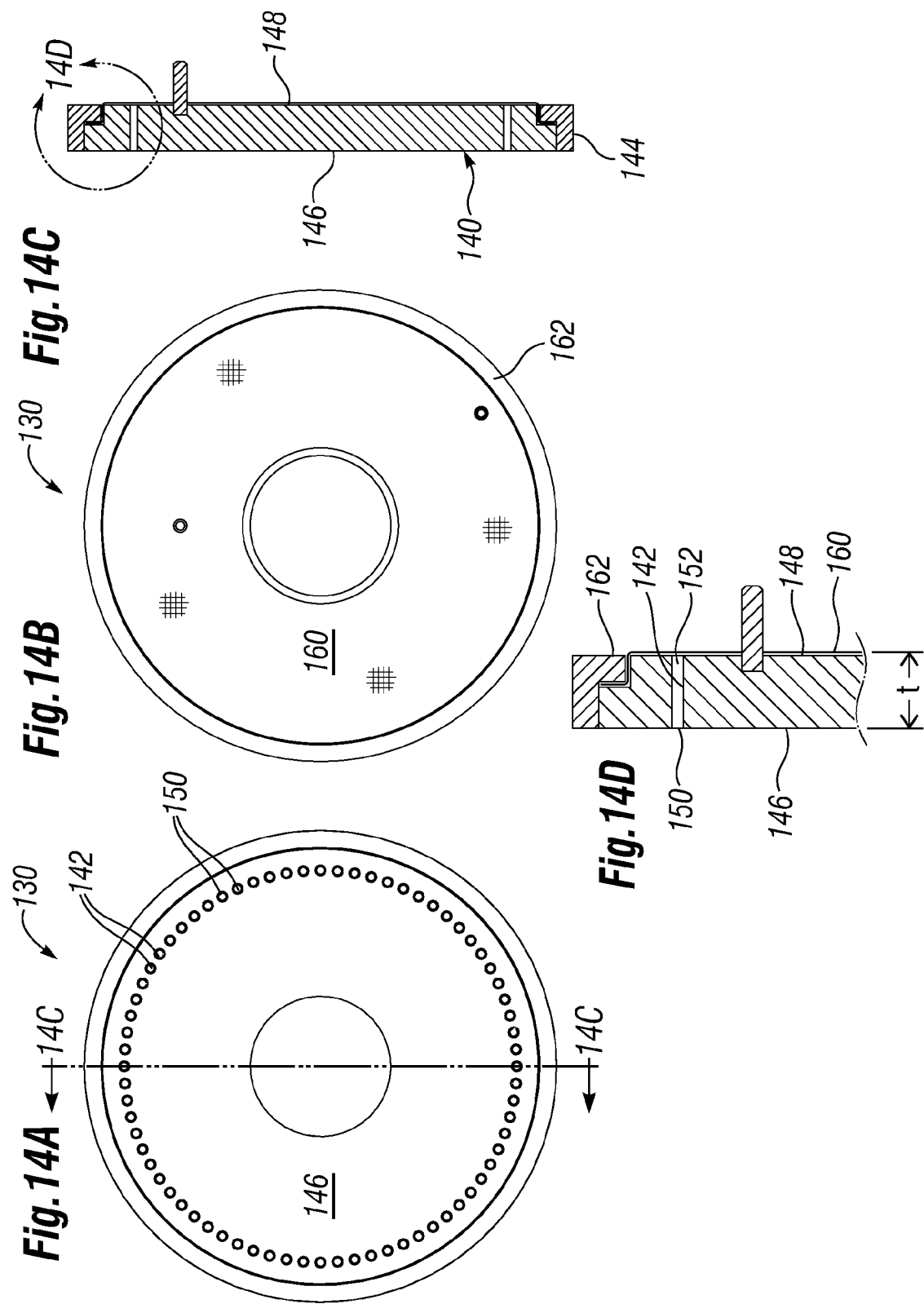

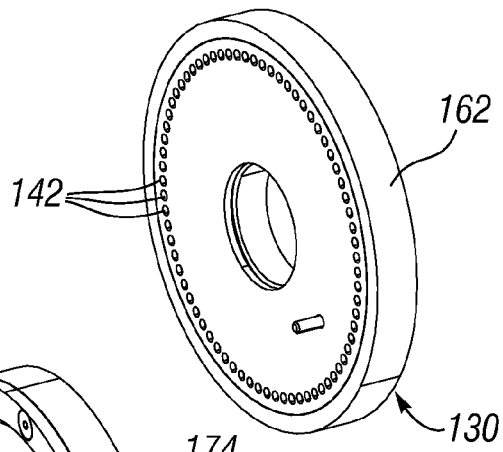
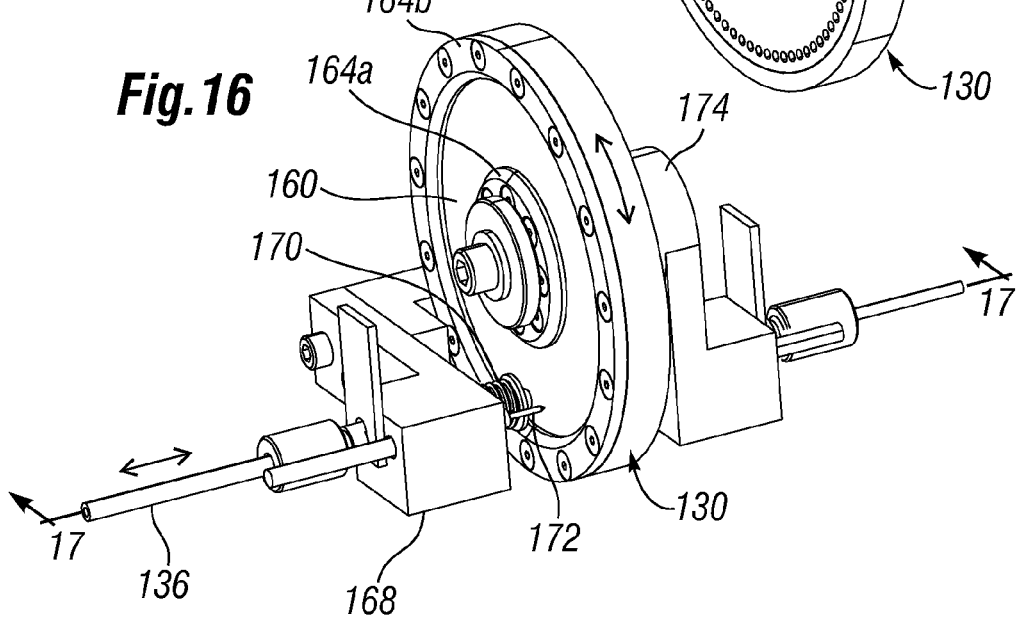
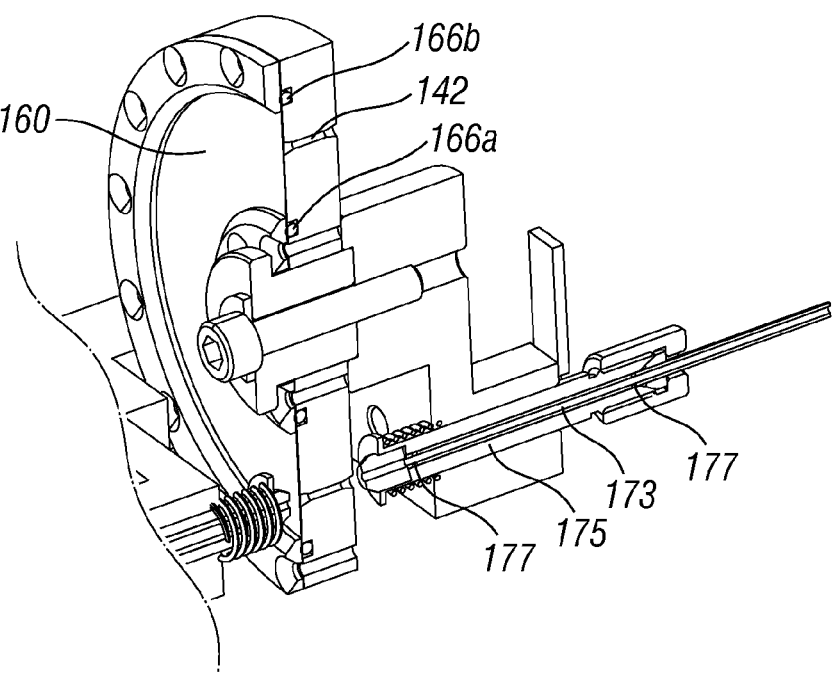

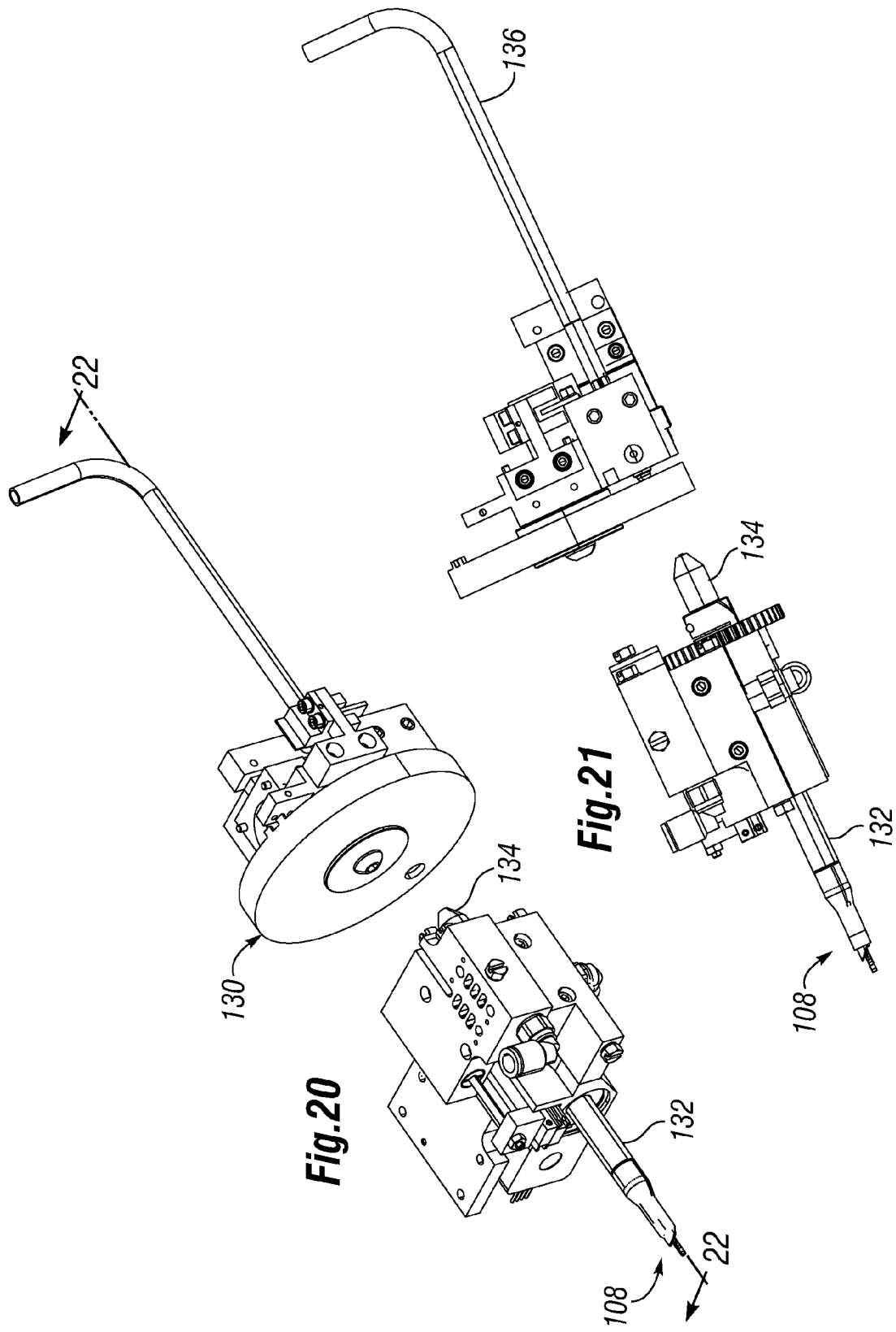

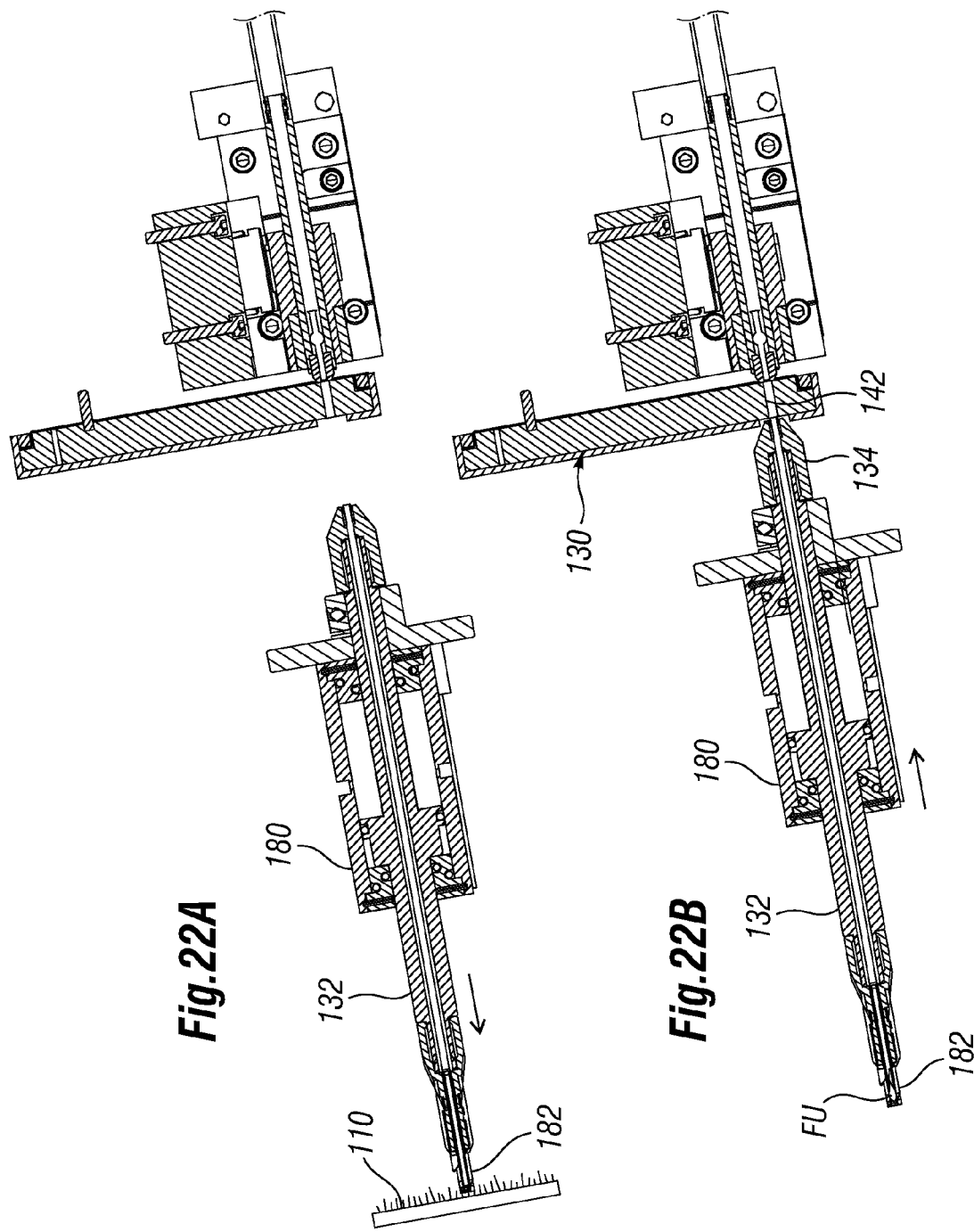

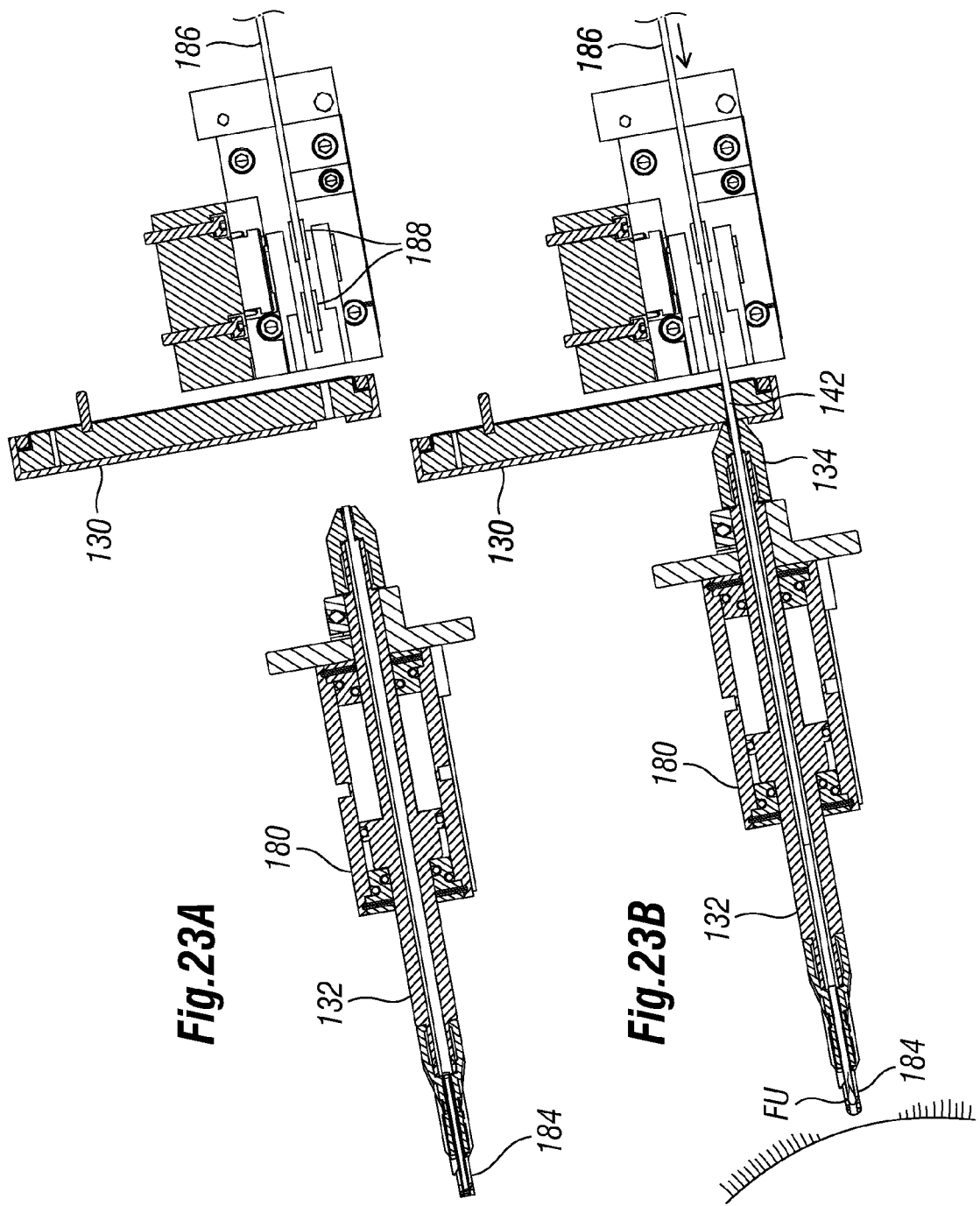

SYSTEMS AND METHODS FOR HARVESTING, STORING, AND IMPLANTING HAIR GRAFTS

CROSS REFERENCE TO RELATED APPLICATIONS

The present application is a continuation of co-pending U.S. patent application Ser. No. 13/541,527, filed Jul. 3, 2012, which is a continuation of U.S. patent application Ser. No. 12/196,524, filed Aug. 22, 2008 and issued as U.S. Pat. No. 8,882,783, which is a continuation of U.S. patent application Ser. No. 12/194,370, filed Aug. 19, 2008 and issued as U.S. Pat. No. 8,211,134, which claims priority to U.S. Provisional Patent Application No. 60/997,188, filed on Sep. 29, 2007, the disclosure of all of which is incorporated by reference herein in its entirety.

FIELD OF THE INVENTION

The present invention relates generally to devices, systems and methods for storing objects used in cosmetic and dermatological procedures, and it is especially useful for storing hair grafts or hair follicles.

BACKGROUND OF THE INVENTION

Various cosmetic and dermatological procedures exist where there is a need to collect and store biological units, for example, for future examination, or processing, or reuse. Hair transplantation procedures are among those well-known procedures, and typically involve harvesting donor hair grafts from the donor areas of the patient's body, most commonly scalp, and implanting them in a bald area (recipient area).

The follicular units may be classified, or "typed," based on the number of hairs in the unit and identified in shorthand as an "F1" for a single hair follicular unit, an "F2" for a two hair follicular unit and so on for follicular units with 3-5 hairs.

Various procedures for hair transplantation have been previously disclosed, including both manual and mechanized to certain degrees of automation. In one well-known manual process, a linear portion of the scalp is removed from a donor area by dissection with a scalpel down into the fatty subcutaneous tissue. The strip is dissected (under a microscope) into the component follicular units, which are then implanted into a recipient area in respective puncture holes made by a needle. Forceps are typically used to grasp and place the follicular unit grafts into the needle puncture locations, although other instruments and methods are known for doing so.

U.S. Pat. No. 6,585,746 discloses an automated hair transplantation system utilizing a robot and various tools maneuverable by the robot to harvest and implant hair grafts.

During manual, semi-automatic, or robotically-assisted procedures for hair transplantation, it is usually desirable to collect and retain harvested follicular units or grafts in some storage device prior to their implantation. Similarly, in other cosmetic and dermatological procedures that require removal of the biological objects or tissue, it may be desirable to collect and store such objects before they are processed, reused or re-implanted. Often these storage devices consist of a container for bulk hair grafts, from which a technician plucks individual grafts for implant. While attempts were made to design some storage devices or cartridges for containing hair follicles for use in manual hair transplantation procedures, there is a clear need for an improved storage device with an improved design and which could be used in manual, partially or fully automated, or robotically-assisted systems and procedures.

SUMMARY OF THE INVENTION

In accordance with a general aspect of one of the inventions disclosed herein, a storage device or a cartridge for holding biological units, for example, follicular units, is provided. The storage device includes a body having a first face and a second face and defining a plurality of receptacles therein for holding biological units. The receptacles each pass through the body from the first face to the second face and include a first opening at the first face of the body and at least one second opening at the second face of the body. A permissive medium covers the second openings of the plurality of receptacles. The permissive medium facilitates movement of a biological unit to or from the receptacles, and may be, for example, meshes, screens, paper, elastomeric materials such as silicone, various resealable materials, etc. The permissive medium prevents biological units from passing into the first opening and exiting the storage device from the second opening, while at the same time allowing passage of air and/or liquids.

In one embodiment the storage device body is substantially cylindrical or disk-shaped and has a thickness dimension along the direction of the cylindrical axis, wherein the receptacles are arrayed in a pattern and through the thickness dimension of the body. The pattern may include at least one circular array of receptacles along a circumference of the storage device, however the pattern may have other configurations, including random, if desired. Alternatively, the body is substantially rectilinear having a thickness dimension and the receptacles are arrayed in a pattern through the thickness dimension of the body. For instance, the receptacles may be arrayed in a close-packed matrix. A pressure relief structure on the receptacles may limit the maximum suction created therewithin.

The permissive medium may comprise a cover attached to the body that extends at least partly over the second face and over the second openings. In one embodiment, each portion of the permissive medium that covers the second openings of the receptacles is rendered unusable once punctured such that the storage device is a single-use device, and is preferably disposable. In another embodiment each portion of the permissive medium that covers the second openings of the receptacles is resealable once punctured such that the storage device may be reused more than once.

In one useful embodiment, the biological unit is a hair graft, and the receptacles are sized to closely receive the hair graft. Furthermore, the storage device may be configured to be removably received in a robotic hair transplantation system. Indeed, the storage device may be configured to be removably received in one or more of a hand-held, partially automated, and fully automated device or system. At least one receptacle of the plurality of receptacles may contain a biological unit preservation solution, and the storage device may be configured to allow for cooling of the biological unit once it is held in a receptacle of the plurality of receptacles.

Another aspect of the invention is a device for transplanting follicular units (FUs) into tissue comprising a robotic system having a robotic arm and a control mechanism, the device also employs a storage cartridge. An implanting tool having a lumen therethrough connects to and is manipulated by the robotic arm. The device includes the cartridge having a plurality of receptacles each adapted to retain an FU. The control mechanism automatically aligns the selected cartridge receptacle with the lumen of the implanting tool and urges the FU from the selected receptacle through the lumen of the implanting tool into the tissue. An obturator positioned to pass through the selected cartridge receptacle may be directed by the control mechanism to urge the FU from the selected receptacle. Alternatively, the control mechanism may initiate a pressure differential through the selected cartridge receptacle to urge the FU from the selected receptacle. In addition, a follicular unit removal tool having a lumen therethrough, may be connected to and manipulated by the robotic arm to position the removal tool over an FU located on a body surface, wherein the control mechanism is adapted to align the lumen of the removal tool with a selected cartridge receptacle and urge the FU through the removal tool into the selected cartridge receptacle.

A still further aspect of the present invention is automated process for shuttling a biological unit such as a follicular unit into and from a storage device having a plurality of receptacles. The process includes at least: acquiring a biological unit into a first tool using substantially automated process; urging the biological unit from the first tool into a selected receptacle of the storage device using a substantially automated process; capturing the biological unit in the selected receptacle; and displacing the biological unit from the selected storage device receptacle into the said first tool or a different tool using a substantially automated process.

In the process, the first tool preferably defines a lumen therethrough and the step of urging the biological unit through the first tool comprises applying a pressure differential to the first tool lumen. Structure may be provided along a path in which the biological unit travels from the first tool to the storage device receptacle to reduce the pressure differential along a portion thereof and thereby reduce the speed of the biological unit along the path. For instance, a parallel flow path outside of the path may be provided which terminates just before the path reaches the storage device. In one embodiment the process includes applying a source of suction to a proximal side of the selected receptacle, and providing a pressure relief channel on the proximal side of each receptacle for limiting the maximum suction created within the receptacle to less than a suction magnitude of the source of suction.

Alternatively, the first tool may define a lumen therethrough and the step of urging the biological unit through the first tool comprises pushing the biological unit through the lumen of the first tool using mechanical means. The process may further include cooling the biological unit while it is stored in the receptacle of the storage device, and preserving the biological unit while it is stored in the receptacle of the storage device with a preservation solution. Preferably, at least some steps of the method are computer-controlled, and at least some steps of the method may be performed by a robot.

In the process, the step of displacing the biological unit from the storage device receptacle may comprise pushing the biological unit from the receptacle using an obturator that passes into the receptacle. In one embodiment, the storage device has a body with a thickness and the receptacles passing through the body between a first opening and a second opening on corresponding first and second ends of the receptacles. Further, a permissive medium covers the second ends of the receptacles, wherein displacing the biological unit from the storage device receptacle comprises pushing the biological unit from the receptacle using an obturator that enters the receptacle through the permissive medium. Alternatively, urging the biological unit through the removal tool comprises applying a pressure differential to the removal tool lumen by reducing the pressure at the second end of the receptacle relative to the first end. For instance, the pressure at the second end of the receptacle is reduced relative to the first end by applying a low pressure source to the second end through the permissive medium, such as by introducing a probe into the receptacle second end through the permissive medium, the probe providing a source of low pressure.

In the process, the step of acquiring may include removing the biological unit from one location on a body surface into the first tool, wherein the first tool is a removal tool, and further implanting the biological unit from the same removal tool or a different tool into another location on the body surface. In one embodiment, the removal tool or said different tool is an implanting tool, the implanting tool defining a lumen therethrough and the step of displacing comprises mechanical pushing of the biological unit into the implanting tool lumen. The process may further include the steps of disengaging the removal tool from the storage device receptacle, and engaging an implanting tool with the storage device receptacle. The process is especially useful when the biological unit is a hair follicular unit.

According to another aspect of the present invention systems and methods for managing biological units (for example, inspecting, classifying, or storing) is provided. In one exemplary embodiment, the system includes a cartridge having a plurality of receptacles each sized to receive a biological unit. An inspection device is operably connected to the cartridge, and the system also includes a mechanism for transferring a biological unit past the inspection device and into one of the plurality of cartridge receptacles. Finally, a processor is provided for receiving signals from the inspection device, and performing one or more of registering passage of the biological unit into one of the plurality of cartridge receptacles, counting biological units, and classifying biological units. The processor is further adapted to record the results of one or more of the operations of registering, counting and classifying for later recollection and selective retrieval from the corresponding cartridge receptacle.

The mechanism that transfers the biological units may comprise an open channel having a pressure differential therein through which the biological units pass. In one embodiment, the inspection device comprises a light source and light detector for registering passage of the biological unit. In a second embodiment, the inspection device comprises a camera for recording an image of the biological unit as it passes the inspection device. The system may further utilize a strobe light arranged to periodically illuminate an imaging point under focus of the camera. A tracking system located upstream of the imaging point adjacent a channel through which the biological units pass may register passage of a biological unit and signal the strobe light to fire. For instance, the tracking system may include light source/detector pairs.

A method of the present invention for managing biological units comprises transferring a biological unit past an inspection device and into one of a plurality of receptacles of a cartridge, each receptacle being sized to receive the biological unit, processing signals received from the inspection device and performing one or more of registering passage of the biological units, counting the biological units and/or classifying the biological units. The method further includes recording the results of one or more of the operations of registering, counting and classifying for later recollection and selective retrieval from the corresponding cartridge receptacle. The step of transferring may involve urging the biological unit through an open channel using a pressure differential. A camera may be used to image each biological unit, and a tracking system for anticipating the position of each biological unit and firing a strobe light may be incorporated.

A system for managing biological units in accordance with another aspect of the present invention includes an inspection device for inspecting a biological unit, a mechanism for transferring a biological unit through the inspection device, and a processor for receiving signals from the inspection device. The processor may also register passage of the biological unit through the inspection device, counts biological units, and/or classifies biological units. The processor is further adapted to record the results of one or more of the operations of registering, counting and classifying. Desirably, the biological unit is a hair follicular unit. The system further may comprise a cartridge having a plurality of receptacles each sized to receive a biological unit, wherein the mechanism for transferring transfers the biological unit past the inspection device and into one of the plurality of cartridge receptacles. The system is adapted for later recollection and selective retrieval of the registered, counted or classified biological unit from the corresponding cartridge receptacle. The mechanism for transferring may be an open channel having a pressure differential therein through which the biological unit passes.

The aforementioned inspection device may comprise a light source and light detector for registering passage of the biological unit. Alternatively, the inspection device comprises a camera for recording an image of the biological unit as it passes the inspection device. A strobe light may be arranged to periodically illuminate an imaging point under focus of the camera. The biological unit may pass through a channel and a tracking system may be provided adjacent the channel upstream of the imaging point, the tracking system is adapted to register passage of a biological unit and signal the strobe light to fire. The tracking system may comprise spaced apart light source/detector pairs connected to relay biological unit position information and the processor may be programmed to calculate when to signal the strobe light to fire.

Additional method for managing biological units of the present invention includes steps of: transferring a biological unit through an inspection device; processing signals received from the inspection device, and performing one or more of the operations of registering passage of the biological unit through the inspection device, counting biological units, and classifying biological units; and recording the results of one or more of the operations of registering, counting and classifying.

In the aforementioned method, the biological unit is desirably a follicular unit, and the method further includes using the inspected follicular unit in a hair transplantation procedure. The method may comprise transferring the biological unit past the inspection device and into one of a plurality of cartridge receptacles, each receptacle sized to receive the biological unit. The method may also include selectively retrieving the biological unit from the corresponding cartridge receptacle based on the recorded results.

Another system of the present invention for managing follicular units comprises a removal tool for removing follicular units from a body surface and transferring each along a pathway from one location to another. The system further includes an inspection device located along the pathway automatically inspects each follicular unit that passes thereby and a processor for receiving signals from the inspection device and registering passage of the follicular unit. The processor may count the number of follicular units that pass by the inspection device, classify each follicular unit that passes by the inspection device, and/or show on a display the classification of each follicular unit as it passes by the inspection device. The removal tool may be connected to a robotic arm and adapted to be manipulated by the robotic arm.

A still further method for managing biological units of the present invention comprises removing a follicular units from a body surface and transferring it along a pathway in a removal tool from one location to another, automatically inspecting the follicular unit that passes along the pathway, and/or processing signals received from the inspection and registering passage of the follicular unit. The method may include automatically counting the number of follicular units inspected, automatically classifying each follicular unit inspected, and/or automatically displaying the classification of each follicular unit classified. The method may further include aligning the pathway with a selected receptacle of a storage cartridge and urging the follicular unit into the selected cartridge receptacle.

A further aspect of the invention provides an automated process for removing from a body surface and storing biological units. The process comprises acquiring a biological unit from the body surface into a removal tool; urging the biological unit through the removal tool into a receptacle of a cartridge; classifying the acquired biological unit; and recording the classification of the biological unit and the location of the corresponding cartridge receptacle for later recollection and selective retrieval. Desirably, the automated process is robotically-assisted.

Other and further objects and advantages of the invention will become apparent from the following detailed description when read in view of the accompanying figures.

BRIEF DESCRIPTION OF THE DRAWINGS

Features and advantages of the present invention will become appreciated as the same become better understood with reference to the specification, claims, and appended drawings wherein:

FIG. 1 is a perspective assembled view of an exemplary cartridge shuttle subsystem of the present invention for harvesting and implanting biological units, such as follicular units;

FIG. 2 is a perspective exploded view of the cartridge shuttle subsystem of FIG. 1;

FIGS. 7A-7E are various perspective, elevational, and sectional views of an exemplary rectilinear cartridge for use with the cartridge shuttle subsystem of FIG. 1;

FIG. 8 is a cutaway perspective view of the exemplary cartridge shuttle subsystem shown in a follicular unit harvesting mode;

FIG. 9 is a cutaway perspective view of the exemplary cartridge shuttle subsystem shown in a follicular unit implant mode;

FIG. 10 is a schematic perspective view of an exemplary robotic biological unit harvesting and implanting system of the present invention;

FIGS. 11-13 are perspective, side and bottom plan views, respectively of a head assembly of the system of FIG. 10;

FIGS. 14A-14D are elevational, and sectional views of an exemplary disk-shaped cartridge for storing hair grafts according to the present invention;

FIG. 15 is a perspective view of the exemplary disk-shaped cartridge prior to loading into a harvesting/implanting system of the present invention;

FIG. 16 is a perspective view of the prepared cartridge of FIG. 15 in proximity to certain harvesting/implanting system components with which it directly interacts;

FIG. 17 is a perspective sectional view of the components of FIG. 16 showing exemplary pressure differential reduction structure in a passage from a harvesting tool to the cartridge to slow down the velocity of a biological unit traveling therethrough;

FIG. 20 is a perspective view of the exemplary embodiment of the follicular unit shuttle components according to the present invention;

FIG. 21 is a side elevational view of the shuttle components;

FIGS. 22A-22D are sectional views through the shuttle components taken along line 22-22 of FIG. 20, and showing a sequence of operation of those components of the one exemplary embodiment of the system for harvesting a follicular unit; and FIGS. 23A-23B are sectional views through the shuttle components taken along line 22-22 of FIG. 20, and showing a sequence of operation of those components of one exemplary embodiment of the system for implanting a follicular unit.

DETAILED DESCRIPTION OF THE PREFERRED EMBODIMENTS

Figure 3:
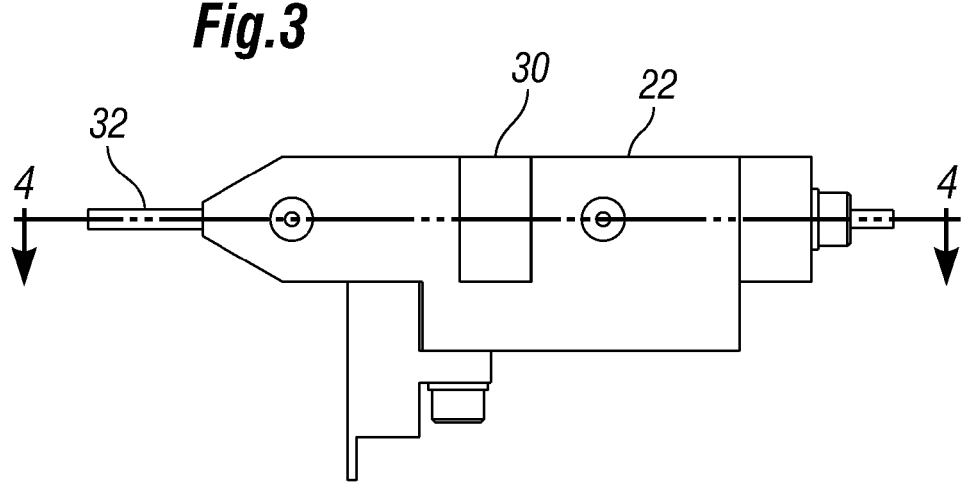
FIG. 3 is a side elevational view of the cartridge shuttle subsystem of FIG. 1.

In the following Detailed Description, reference is made to the accompanying drawings, in which are shown by way of illustration specific embodiments in which the invention may be practiced. In this regard, directional terms such as "top," "bottom," "front," "back," "distal," "proximal," etc., are used with reference to the orientation of the Figure(s) being described. Because components or embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following Detailed Description, therefore, is not to be taken in a limiting sense, and the scope of the present invention is defined by the appended claims.

The adjective "automated" with reference to a system or process as a whole means that some part or all of a particular system or step in the process involves an autonomous mechanism or function; i.e., that mechanism or function does not require manual actuation. Ultimately, one or more steps in the procedure may be automated, or autonomous, with some parts requiring manual input. This definition encompasses an automated system that requires only an operator to depress an ON switch or schedule the operation, and also a system in which hand held tools are used but some mechanism of the system functions autonomously, i.e., without human input, to perform a function. Some of the automated processes described herein may also be robotically-assisted or computer/software/machine-instruction controlled. The devices and methods of the present invention are useful in manual procedures and systems, as well as in automated procedures and system, and they are especially useful in the robotically-assisted systems and procedures. In contrast, the adverb "automatically" when referred to use of a particular component of a system or a particular step in a process means that such step is accomplished autonomously, i.e., without real-time manual assistance.

The term "tool" as used in harvesting (or removal) tool with reference to a hair transplantation procedure refers to any number of tools or end effectors that are capable of removing or harvesting FUs from a body surface. Likewise, a "tool" as used in implanting tool with reference to a hair transplantation procedure refers to any number of tools or end effectors that are capable of implanting/inserting FUs to a body surface. In this sense, a body surface can be attached to the body or be a flap of skin removed from the body. Such tools may have many different forms and configurations. In some embodiments, the tool comprises a hollow tubular shaft. The distal end of removal tools (for example, punches, coring devices, cutting and/or trimming devices, needles), are typically sharpened, to cut and extract the tissue (e.g., hair follicle). Implanting tools may also be sharpened so as to perform puncture and delivery of the FU in one operation. However, the puncture may be formed by another tool, with the implanting tool being relatively blunt and used just for delivery of the FU. It also should be noted that the harvesting and implanting tools could be the same or different instrument, depending on the procedure and objects to be removed or harvested.

The present invention utilizes a storage device into which harvested biological units are placed. The storage device includes receptacles for receiving the biological units and may be immediately reused to present the biological units for implantation, or may be retained for a period for later use. In one preferred embodiment, the storage device comprises a body having a thickness dimension and the receptacles extend through the body along the thickness dimension. The storage device may be alternately referenced herein as a cartridge or storage cartridge. It should be understood that the exemplary storage devices (e.g., a cartridge for hair follicles) of the present invention are especially suited for use with a robotic system or computer-controlled system. However, certain principles of the storage devices also provide improvements that could be used with manual, other automated or partially automated systems and devices.

"Biological units" includes discrete units used in cosmetic and dermatological procedures, for example, various tissue, including that extracted for biopsies or grafting, skin units, etc. One example of the biological units particularly useful with the present invention are hair grafts, or follicles, or "follicular unit(s)."

The present invention discloses an entire system, a shuttle subsystem component thereof, and the storage device useful for harvesting and implanting biological units. As mentioned above, the term biological units encompasses a number of things, though the present invention is particularly useful in robotic hair transplantation, to provide an automated system and a storage device for harvesting and implanting follicular units (FUs). As such, the term follicular units (or FUs) will be used herein simply as an example for purposes of describing some embodiments of the present invention with the understanding that it represents more broadly biological units. An exemplary shuttle subsystem will be described first, and an entire system second, and it should be understood that the robotic principles and mechanism that are described with respect to the entire system could be adapted to utilize the earlier-described subsystem.

According to the one aspect of the present invention, FIGS. 1-9 illustrate various components and process steps for an exemplary cartridge shuttle subsystem 20. This shuttle subsystem "shuttles" or transfers hair grafts from the body surface and/or harvesting tool into the cartridge and back from the cartridge into an implanting tool. With reference to FIGS. 1 and 2, the subsystem 20 comprises a block-like base member 22 having a distal end 24 and a proximal end 26. A longitudinal direction will be defined extending from the distal end 24 to the proximal end 26, while the transverse direction extends perpendicular thereto in a horizontal plane. The base member 22 defines a transverse channel 28 that receives therein a rectilinear cartridge 30. The cartridge 30 slides transversely within the channel 28 either manually or automatically, for example, under the control of a robotic manipulator (not shown).

A tool 32 extends distally from the distal end 24 of the base member 22. The illustrated exemplary tool 32 for convenience and simplicity schematically represents both an FU removal/harvesting tool and an implanting tool, which can be interchangeably coupled to the base member 22. Typically, the harvesting tool includes a coring distal end, and both a harvesting tool and an implanting tool typically define therein a lumen or throughbore. An elongated rod-like obturator 34 projects proximally from the proximal end 26 of the base member 22. The use of the obturator 34 will be described below. The cartridge shuttle subsystem 20 further preferably includes an inspection device 36. The inspection device 36 may be used in variety of ways. It could simply register the passing of the harvested FU from the harvesting tool into the cartridge, or from the cartridge back into the implanting tool to verify that an FU was successfully removed and transferred into the cartridge. Furthermore, the inspection device 36 could be used for purposes of counting the number of FUs that are transferred; or in more advanced systems, it may also allow for assessment or classification of, for example, the size and/or character of harvested follicular units.

Figure 4:
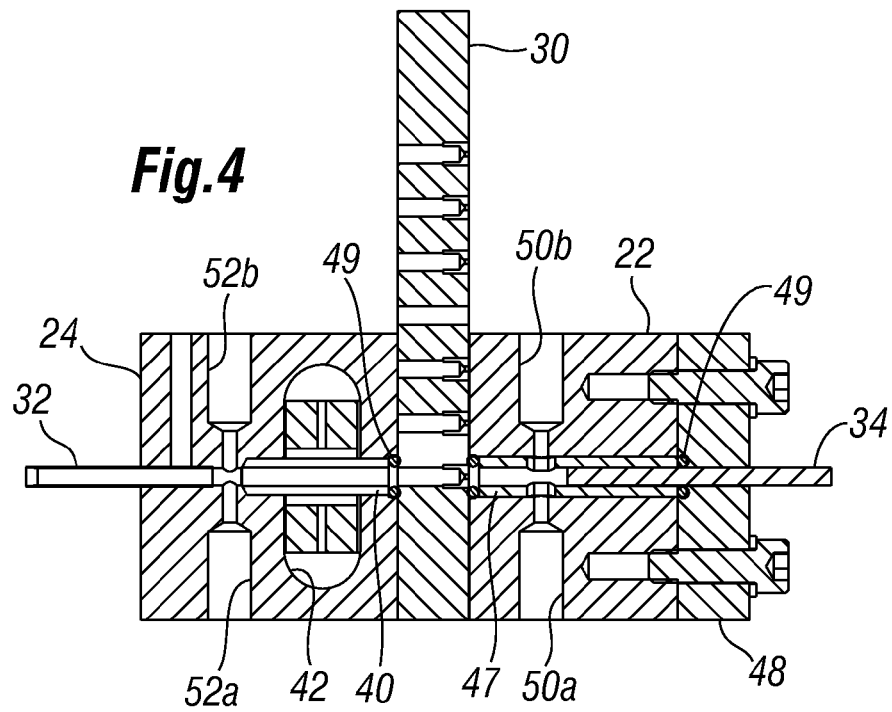
FIG. 4 is a sectional view through the cartridge shuttle subsystem taken along line 4-4 of FIG. 3 and showing a number of flow ports therethrough.

With reference now to FIG. 4, the base member 22 defines a longitudinal channel extending entirely through the body substantially along the midline thereof. On the distal end 24 the channel receives the tool 32 such as in an interference fit or with mutual threading. Just proximal to the tool 32, a transparent inspection tube 40 defines a throughbore that provides a continuation of the longitudinal channel across a gap 42 in the base member 22. As seen in FIG. 2, the inspection device 36 includes a pair of vertically-oriented fingers 43 that extend into the gap 42 and flank the inspection tube 40. The fingers 43 contain sensors, such as light detectors, or cameras, etc., for inspecting and/or registering the FUs that travel through or pause in the inspection tube 40.

In one very simple and useful mode of operation, the inspection device 36 comprises an LED transmitter and receiver combination in the fingers 43. When an FU traverses the inspection tube 40, the LED light beam is interrupted, which is sensed by the receiver. This signals to the system that an FU has passed. If during one harvesting step no FU is sensed, the system processor records the absence of an FU in that particular receptacle of the cartridge, and the receptacle, for example, may then be skipped in a subsequent implant sequence using that cartridge.

Another exemplary means of inspecting FUs is an imaging system that acquires an image of any one follicular unit and utilizes image processing to assess, for example, the type, size of the FU and/or number of follicles therewithin, as well as to count them. Various ways to inspect and classify FUs are disclosed in two PCT applications directed to systems and methods for classifying and counting FUs, PCT/US07/76726 and PCT/US07/76728, both filed on Aug. 24, 2007. These applications are expressly incorporated herein by reference. As will be explained below, in yet another aspect of the present invention, the storage device or cartridge of the present invention could be used in conjunction with the systems described in these two PCT applications to provide information about the type of hair follicle unit located in selected receptacles in the cartridge 30. Various means of classifying could be used depending on the biological unit. For example, hair could be classified based on whether it is a multiple or single hair unit, while for other biological units the scheme could be their size, shape, chemistry, etc.

In one preferred embodiment, the system of the present invention includes a processor for receiving signals from the inspection device 36 and the mechanism for transferring a biological unit into a known cartridge receptacle. The processor classifies the biological unit and records the classification for later recollection and selective retrieval from the corresponding cartridge receptacle. For instance, the inspection device 36 may include an image acquisition device, and the processor is an image processor configured for processing an image obtained by the image acquisition device. As described in PCT/US07/76726 and PCT/US07/76728, the image processor may be configured for counting and/or classifying the FU, including for example, calculating a contour of the segmented image of the FU, calculating an outline profile of the segmented image which disregards concavities in the calculated contour of the segmented image of the FU, determining the number of defects in the outline profile, and finally classifying the FU at least partially based on the number of determined defects. Alternatively, the image processor may be configured for recording or registering the FU.

Of course, various image acquisition devices could be used, represented by the inspection device 36, such as those described in PCT/US07/76726 and PCT/US07/76728. For example, the image acquisition device may be one or more cameras, such as any commercially available cameras. Or, the image acquisition device could be a video recording device (such as a camcorder). While it is preferred that the image acquisition device be a digital device, it is not necessary. It could be, for example, an analog TV camera that acquires an initial image which is then digitized into a digital image. The image processor may comprise any device programmed and configured to perform the method of registering, counting, and/or classifying a biological unit (e.g., an FU). One non-limiting example of a suitable image processor is any type of personal computer ("PC"). Alternatively, the image processor may comprise an Application Specific Integrated Circuit (ASIC) or Field Programmable Gate Array (FPGA). The image processor may be programmed with software configured to perform the methods of the present invention.

To obtain better images of the follicular units to allow for inspection, assessment and registering of the FUs, the present invention also provides components for tracking or monitoring the position of the FU as it "shuttles" or transfers from the body surface and/or harvesting tool into, for example, a storage cartridge, such as through the exemplary shuttle subsystem 20. Alternatively, FUs may be imaged and inspected as they pass through the inspection device prior to their implantation without any use of a storage cartridge. In such applications, the inspected biological units, such as FUs, may be classified and then immediately implanted into a desired location based on the results of the inspection and/or classification. Various embodiments, including those with or without the use of a storage cartridge may be employed using similar techniques, as described below. In general, an inspection device assesses each FU (or a sampling of FUs) as it moves through the shuttle subsystem 20. In this respect, a mechanism is used to transfer the FUs (or more generally biological units) past the inspection device and, for example, into one of the plurality of cartridge receptacles in those embodiments where the cartridge is used. It should be understood that the mechanism for transferring the FUs may be the open channel with a pressure differential, as described above, or another such mover like a conveyor, pick and place, or similar expedient.

Figure 5:
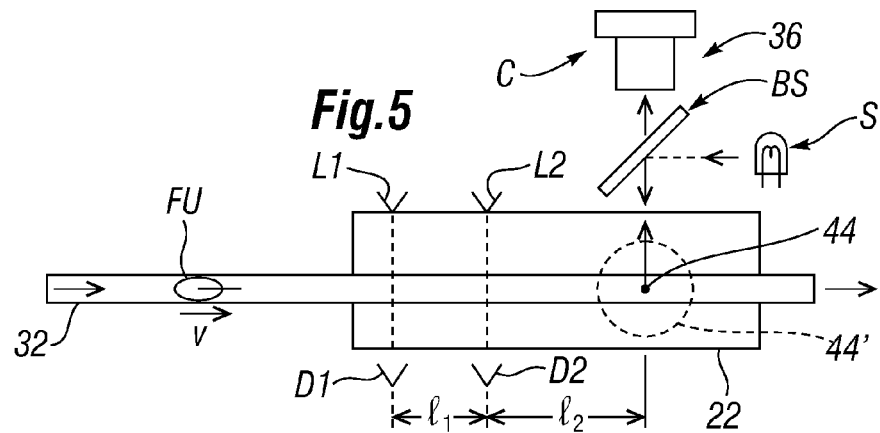
FIG. 5 is a schematic diagram of a portion of one embodiment of a cartridge shuttle subsystem with an exemplary follicular unit inspection device.
Figure 6A:
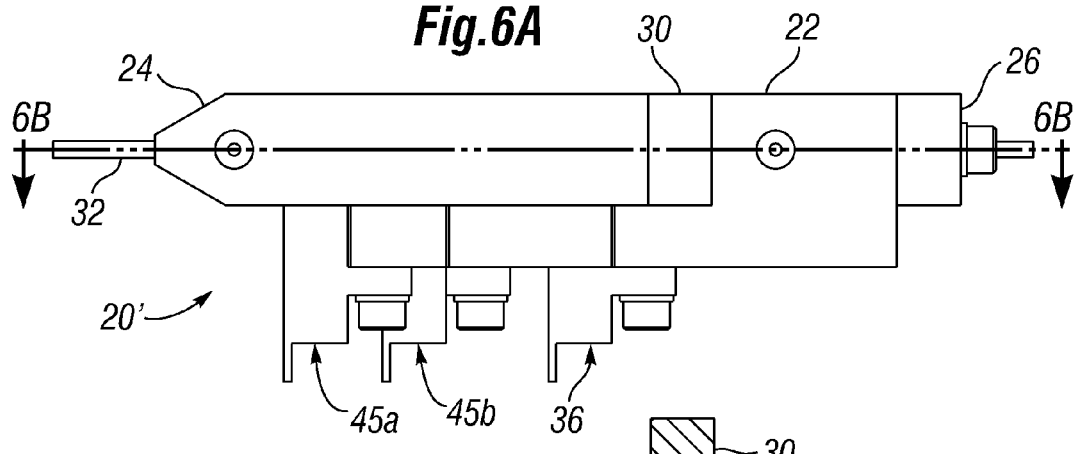
FIGS. 6A and 6B are side elevational and sectional view through an exemplary cartridge shuttle subsystem with the inspection device of FIG. 5.
Figure 6B:
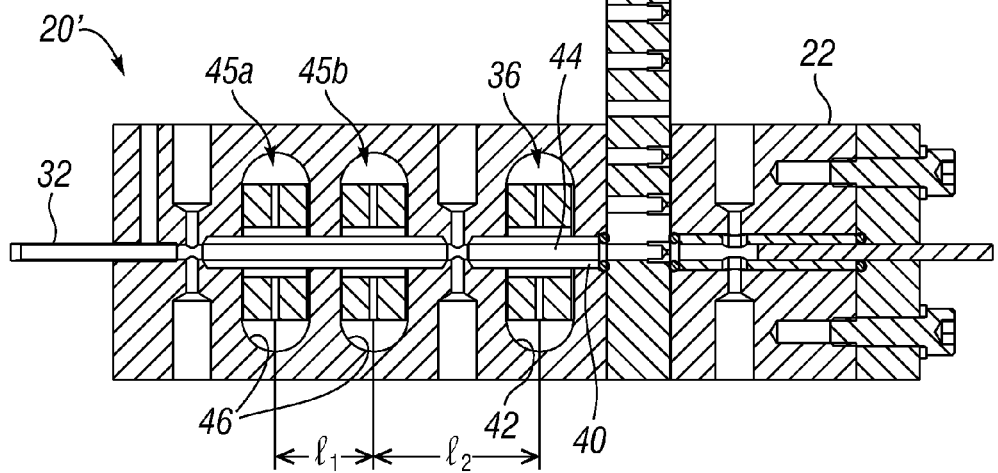

By anticipating/calculating the position of the FU as it moves through the subsystem, or by stopping the FU's motion in the field of view of the camera, a strobe light may be fired at a point and time where a camera can obtain a clear image. Generally, an imaging device (e.g. camera) may make an image of an FU as it travels to or from the cartridge. In order to do it, a tracking system located adjacent the channel through the shuttle subsystem 20 upstream of an imaging point may be used to detect the FU's presence in the shuttling system and measure its velocity. The tracking system in conjunction with a processor/controller may use the velocity information to strobe a lamp at the instant the FU is within the field of view of the imaging device. The strobe may freeze the motion of the FU for observation and inspection. Alternatively, the FU can stop its motion in the field of view of the camera and have its image recorded. For instance, FIG. 5 schematically shows components for tracking/registering the movement of a biological unit such as an FU in the systems of the present invention. For reference purposes, these components may be incorporated into the subsystem 20, and therefore like elements will be given like numbers. Indeed, FIGS. 6A and 6B are side elevational and sectional view through a modified cartridge shuttle subsystem 20' with the addition of FU tracking components. This technique for monitoring, registering, inspection, and assessment of an FU of interest may also be useful in a handheld device for harvesting FUs, and illustration in the automated subsystem 20' should not be considered limiting.

In exemplary FIG. 5, an FU is shown traveling at a velocity v through the lumen of a harvesting tool 32 that projects distally from the distal end of the base member 22. As described above, the lumen of the tool 32 leads into a longitudinal channel extending through the base member 22 and past an imaging point 44 aligned with an inspection device 36. The inspection device 36 in the illustrated example includes a camera C, a strobe S, and a beam splitter BS. The strobe S is shown aligned with the camera axis, although it may also be misaligned. Prior to reaching the imaging point 44, the FU passes between a first or upstream checkpoint comprising a first light source $L_1$ and a first light detector $D_1$, and a second or downstream checkpoint including a second light source $L_2$ and a second light detector $D_2$. The first and second checkpoints register passage of the FU when it breaks the continuity of light transmission between the respective source and detector. A processor/controller receives inputs from these sensors and sends outputs to each of the various instruments, and includes a memory.

The processor/controller may be adapted to receive signals from the inspection device, and performing one or more of the additional operations, including but not limited to registering passage of the biological unit through the inspection device and into one of the plurality of cartridge receptacles in those embodiments including the cartridge, counting biological units, and classifying biological units. Further, the processor/controller may record the results of one or more of the operations of registering, counting and classifying for later recollection and selective retrieval from the corresponding cartridge receptacle.

Although systems and methods of the present invention are considered particularly useful for effectively managing/processing a plurality of biological units in sequence, such as by classifying and/or storing them in select receptacles in a cartridge, various concepts described herein are also applicable for more manual one-by-one biological unit management. For instance, an inspection device may be coupled to a manual or partially automated hand-held biological unit removal tool for real-time assessment of each biological unit. For example, such a follicular unit removal tool may incorporate an inspection device that displays to the user the type of FU (e.g., F1, F2, etc.). The user can then easily determine the subsequent action, such as by implanting the FU in the appropriate location, or expelling the FU into a container holding those types of follicular units. In addition, such a tool and inspection device could be coupled to the processor/controller which keeps track of the number of different types of FUs that have been removed. In other words, although the various systems described herein are extremely useful for automated or robotic biological or follicular unit removal/management/implantation, they are also useful and desirable in conjunction with hand-held or other manual non-robotic tools.

With reference again to FIG. 5, the distance between the first checkpoint and the second checkpoint is indicated as $l_1$, while the distance between the second checkpoint and the imaging point 44 is indicated as $l_2$. The time $\Delta t_1$ that the FU takes to travel between checkpoints is recorded, and the velocity v of the FU can be calculated using the formula:

$$v = l_1 / \Delta t_1$$

Subsequently, the time $\Delta t_2$ that the FU takes to travel between the second checkpoint and the imaging point 44 can be calculated using the formula:

$$\Delta t_2 = l_2 / v$$

The controller then triggers the strobe S at a time $\Delta t_2$ after the FU passes the second or downstream checkpoint, and instructs the camera C to take a picture of the imaging point 44. With proper response times, the FU will be centered at the imaging point 44, or at least within the camera's field of vision 44', at the time the strobe S fires and the camera C takes a picture. This system thus ensures that a clear image of each FU can be obtained. Information from the images of the FUs can then be used for multiple purposes, including without limitation: registering passage of each FU through the shuttle system, counting the number of FUs, including those sent to the cartridge, classifying and sorting FUs, such as based on its size, character, the number of hairs therein (e.g., "F1" for a single hair follicular unit, "F2" for a two hair follicular unit, and so on), or keeping track and recording information on the type of an FU contained in each receptacle of the cartridge. Because of the relatively constant suction and therefore velocity v of the FUs passing through the system, the time deltas between the checkpoints and the imaging point 44 also remain fairly constant, which further ensures success of the image collection by eliminating transients. Moreover, an operator may sample the images and adjust the timing slightly if the FUs are not precisely centered at the imaging point 44.

FIGS. 6A and 6B illustrate a modified shuttle subsystem 20' with the addition of FU tracking components. As provided in the original embodiment of FIGS. 1 and 2, the subsystem 20' comprises a block-like base member 22 having a distal end 24 and a proximal end 26. A longitudinal direction extends from the distal end 24 to the proximal end 26, while the transverse direction extends perpendicular thereto in a horizontal plane. A transverse channel in the base member 22 receives a rectilinear cartridge 30 that slides either manually or automatically, for example, under the control of a robotic manipulator (not shown). An exemplary removal/harvesting tool 32 extends distally from the distal end 24 of the base member 22.

FIG. 6B shows the subsystem 20' in horizontal cross-section, and as in FIG. 4 shows a gap 42 in the base member 22 within which is positioned the inspection device 36. It should be noted that the inspection device 36 schematically represents the assembly of the camera C, a strobe S, and a beam splitter BS as described above with respect to FIG. 5. The base member 22 also receives first and second checkpoints 45a, 45b within corresponding spaces 46. As described above, the checkpoints 45a, 45b each desirably include a light source and light detector positioned to sense longitudinal passage of a FU through the subsystem 20'. As in the schematic of FIG. 5, the upstream and downstream checkpoints 45a, 45b are spaced apart a distance 4, while the downstream checkpoint 45b is spaced from the imaging point 44 a distance $l_2$.

The cartridge 30 includes a plurality of receptacles for receiving FUs. As each FU is inspected and identified by the device 36, the controller can manipulate the cartridge 32 to place particular FUs within particular receptacles, or simply catalog the contents of the receptacles of the cartridge. For example, all of the F1 FUs may be placed in one select group of receptacles, while the F2 and larger FUs will be placed in the rest of the receptacles.

Still with reference to FIG. 4, the longitudinal channel through the middle of the base member 22 continues across the transverse channel 28 (as seen in FIG. 2) through one of a number of receptacles formed in the cartridge 30. A tubular sleeve 47 defines a throughbore that forms a distal section of the longitudinal channel. The tubular sleeve 47 fits within a bore formed in the base member 22 and is secured therein with a cover 48 that is bolted to the base member. The obturator 34 is shown closely fit within the throughbore of the tubular sleeve 47. A plurality of O-rings or seals 49 shown in FIG. 4 prevent fluid leakage from the various sections of the channel and the exterior.

The base member 22 defines a plurality of transverse fluid ports that intersect the longitudinal channel. Specifically, a pair of proximal ports 50a, 50b extend from opposite sides of the base member 22 and converge in the middle, registering with a pair of side ports 51 (see FIG. 2) in the tubular sleeve 47. A pair of distal ports 52a, 52b extend from opposite sides of the base member 22 and converge in the middle in fluid communication with a small section of the longitudinal channel between the tool 32 and the inspection tube 40. The ports 50, 52 receive connectors (not shown) of sources of fluid or vacuum. Therefore, as will be explained below in the description of use of the subsystem 20, differential pressures may be created along the longitudinal channel. Preferably, the fluid used to pressurize the subsystem 20 is saline, although air may also be used. For hair follicles, saline is preferred to help maintain hydration of the FUs during the harvesting and/or implant procedure. However, any other preservation solutions are equally useful in the present invention. Use of a preservation solution is advantageous as each receptacle desirably contains some of the preservation solution after being filled with an FU. Moreover, to better preserve FUs, the preservation solution may be cooled or chilled as desired.

According to another aspect of the present invention, a storage device or cartridge 30 is provided. Such cartridge preferably has a high density of holes or receptacles to store FUs (or other appropriate biological objects) in small spaces. Moreover, such cartridge preferably permits storage of FUs under a controlled environment, for example, keeping them sterile, or moist, or at a desired cool temperature. The shape or configuration of the storage device or cartridge 30 may take many forms, and neither the rectilinear or later-described cylindrical or disk-like shapes are necessary or limiting, and can vary according to the intended application. The storage devices of the present invention are advantageously configured to define a plurality of receptacles for receiving the biological units. Such storage devices can be manipulated to register each receptacle, for example, sequentially with harvesting and/or implanting tools. Preferably the storage devices are small enough to be easily exchanged within the overall subsystem or system, and easily sterilized if they are to be reused. Alternatively, the storage devices may have certain features which prevent reuse, and thus they are disposable.

FIGS. 7A-7E illustrate a number of views of one exemplary rectilinear cartridge 30 for use with the subsystem 20. FIG. 7A shows a distal face (or first face) 60 while FIG. 7B shows a proximal face (or second face) 62. The faces 60, 62 are planar and rectilinear, and lie in parallel. Some non-limiting examples of the rectilinear cartridges are those shaped like squares or rectangles. A thickness dimension t shown in FIG. 7B extends perpendicular to the faces 60, 62. A plurality of receptacles 64 extend entirely through the cartridge 30 from the distal face 60 to the proximal face 62. Each of the receptacles 64 defines a first opening 66 at the distal/first face 60, and a pair of second openings 68 at the proximal/second face 62. The precise exemplary shape of the receptacles 64 of this embodiment is seen in cross-section in FIGS. 7D and 7E, and may be easily formed, for example, by drilling one large hole from the distal face 60, and two smaller holes from the proximal face 62. The cartridge 30 further defines a plurality of indexing notches 70 along an upper edge on the proximal side. The notches 70 can be used to displace the cartridge 30, or as location indicators for each of the receptacles 64. In addition to the receptacles 64, a central bore 72 having a constant diameter extends between the faces 60, 62. As will be described below, the bore 72 permits passage of the obturator 34 through the cartridge 30.

FIGS. 8 and 9 illustrate two stages in a process for first harvesting and then implanting an FU. The FU is shown in FIG. 8 in proximity to the tool 32. In the exemplary embodiment, the tool 32 is designed for removing the FU from a body surface, and may include a sharp distal tip or any other structure for grasping and removing the FU. Notice transverse placement of the cartridge 30 so that a first or any other desired receptacle 64 on one end registers with the longitudinal channel. This places the receptacle 64 in fluid communication with the longitudinal channel, and with the ports 50, 52. The operator or an automated system manipulates the shuttle subsystem 20 so that the FU enters a lumen 74 of the tool 32. For example, the operator may cause the tool 32 to plunge into a body surface around the FU.

Once the FU is within the lumen 74, the tool 32 is retracted from the body surface and a pressure differential applied through the lumen 74 to cause the FU to translate in a proximal direction toward the receptacle 64. The pressure differential along the longitudinal channel is controlled by the relative pressures of fluid at the ports 50, 52. As the FU passes the inspection tube 40, the inspection device 36 registers, counts, and/or classifies it. Desirably the FU continues at a constant rate through the longitudinal channel into the receptacle 64. Alternatively, the FU may be caused to pause in or slow down through the inspection tube 40 so that the inspection device 36 obtains a sufficient image for classification purposes.

In various embodiments, the FU monitoring components seen in FIGS. 5 and 6A-6B (or other alternative components designed to achieve similar result or function) may be used to monitor the position of the FUs passing through the longitudinal channel, and in particular when each FU passes the inspection device 36 that includes an imaging device, such as a camera. An image of each FU may be analyzed in real-time to determine, for example, the character, count, size, and other characteristics of the FU, which is then further processed accordingly, such as by aligning the cartridge 30 along the transverse channel 28 to position a selected receptacle to receive the FU.

The end of travel of the FU is at the proximal end of the first receptacle 64. By virtue of the pair of second openings 68 on the proximal end of the receptacle, fluid passes therethrough but the FU does not. The speed of the FU as it approaches the receptacles 64 may be reduced by providing parallel flow channels (not shown), or through various structural means, some of which are described in reference to another embodiment below.

At this stage, the FU has been stored in the receptacle 64. The system or operator then indexes the cartridge 30 along the transverse channel 28 to position one of the other receptacles into registration with the longitudinal channel, and the process of harvesting an FU is repeated. When all or any of the desired receptacles 64 contain FUs, the cartridge 30 may be removed until it is ready for use in implanting the FUs back into a body surface of a recipient. Indeed, a plurality of cartridges 30 may be filled before the implant procedure. Or, the FUs stored in each cartridge may be immediately implanted without changing the cartridge.

It should be noted that the linear pattern of receptacles 64 in the cartridge 30 is exemplary only, and any number of receptacle patterns may be utilized. Of course, if the receptacles 64 are not aligned linearly then the cartridge will have to be displaced in at least two directions to register each receptacle with the longitudinal channel through the subsystem 20. Also, a close-packed matrix that does not consist of regularly spaced perpendicular rows may be used.

In a first step in the implant procedure, a cartridge 30 that has receptacles filled with FUs is positioned within the base member 22 and one of the receptacles 64 registers with the longitudinal channel. Shuttling of the hair follicles from the cartridge to the implant tool could be accomplished using various approaches. In some embodiments, a pressure differential in the distal direction may urge the FU out of that receptacle and into either the inspection tube 40 or implant tool 32. For example, the vacuum tube 136 described above that creates a pressure differential urging the FU in the proximal direction can also be used to reverse the pressure differential to propel the FU distally. The reader will understand that the implant tool 32 may be the same as the harvesting tool previously used, but is typically configured differently, thus requiring a change out.

In other embodiments, the FU may be pushed from the cartridge into the implant tool using, for example, a mechanical device such as obturator, as shown in FIG. 9. FIG. 9 illustrates the cartridge 30 having been transversely displaced to register the bore 72 with the longitudinal channel. At this stage, the operator or system causes the distal end of the implanting tool 32 to enter the body surface of the recipient. To accomplish this, the distal end of the implanting tool 32 may be sharpened, or the tool may be introduced into a previously formed puncture or incision. The operator or system then translates the obturator 34 entirely through the longitudinal channel, thus pushing the FU out of the tool 32. In other alternative embodiments, a combination of mechanical pushing and pressure differential could be used to expel FU from the cartridge.

FIG. 10 is a schematic perspective view of an exemplary robotic biological unit harvesting and implant system 100 according to another aspect of the present invention. The system 100 includes a robotic arm 102 having a head assembly 104 mounted for rotation on a down tube 106 of the robotic arm. Various arrows are shown to illustrate the movement capabilities of the system 100. Furthermore, as will be seen below, motors and other such movement devices incorporated in the head assembly 104 enable fine movements of an operating tip 108 in multiple directions.

The operating tip 108 is shown positioned over a body surface 110, in this case a strip of tissue having hair follicles thereon. A personal computer 112 acting, for example, through a robotic control 114 controls the various movement devices of the robotic arm 102 and head assembly 104. The control system or mechanism 114 may be operatively coupled to the robotic arm and configured to control the motion of the robotic arm, including the motion based on the images or data acquired by any image acquisition device that could be used with the system. Alternatively, all processing and controls of all movements of all the tools, including harvesting and implanting tools, the robotic arm and any other moveable parts of the assembly, and those based on the images or data acquired by the image acquisition device, may be incorporated in one processing and control system, such as 114. An operator monitors conditions and provides instructions through a monitor 115, keyboard 116, and mouse 118. A magnified image of the body surface 110 can be seen on the monitor 115.

Figure 12:
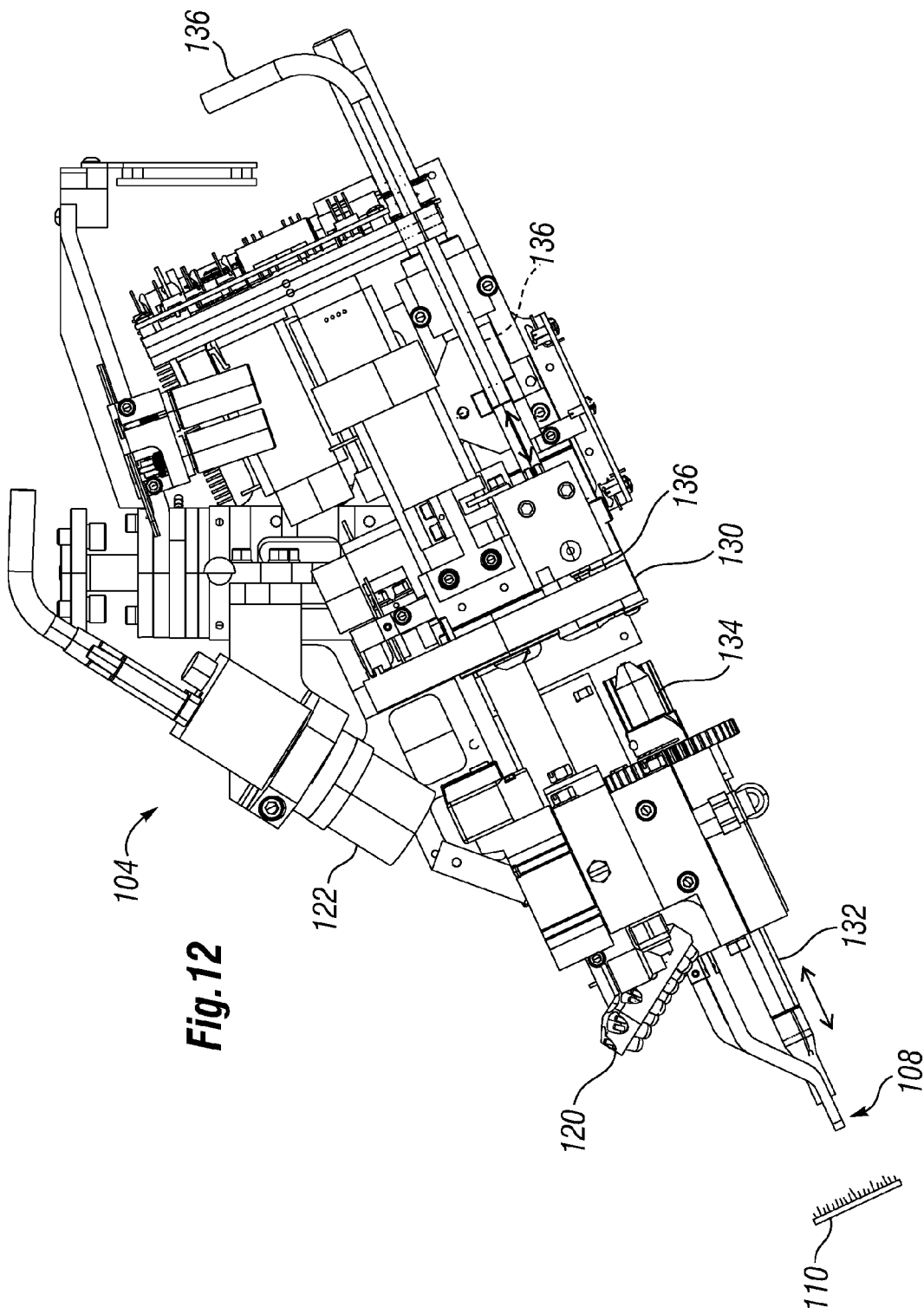
Figure 13:
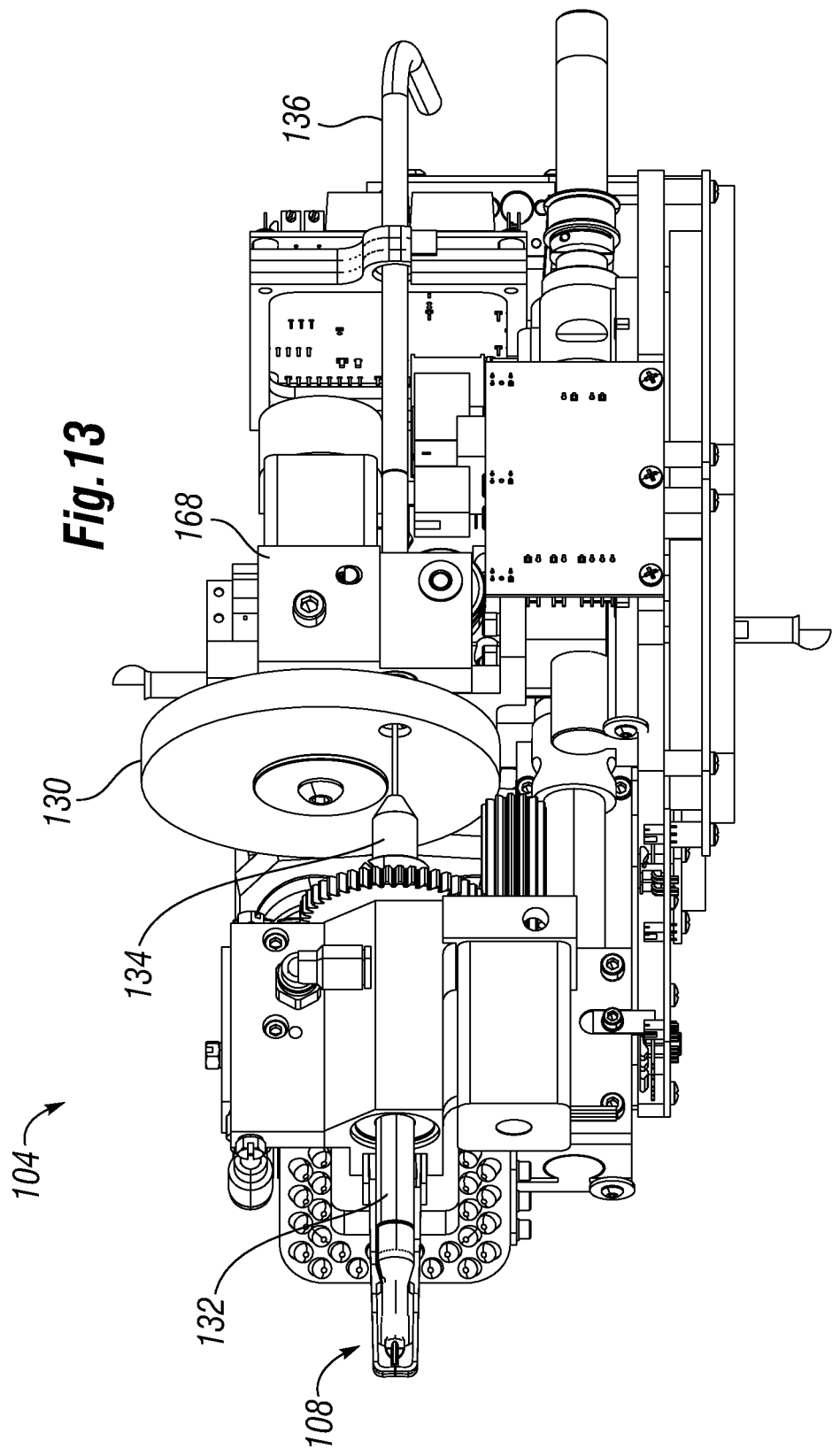

FIGS. 11-13 are perspective and elevational views of the head assembly 104 of the system 100. The side view of FIG. 12 shows the body surface 110 in proximity to the operating tip 108. A bank of LEDs 120 illuminates the body surface 110 so that an imaging device, which is a pair of cameras 122 in the illustrated embodiment, obtains a clear picture for transmission back to the monitor 115. A plurality of circuit boards 124 mounted on the left side of the head assembly, as looking from the operating tip 108, provides real-time control of the various subsystems thereon. Various components are mounted for rotation or linear translation relative to the down tube 106 of the robotic arm 102. Stepper motors, hydraulic cylinders, and the like may be used, and will not be described in great detail herein.

FIGS. 11-13 illustrate a cylindrical cartridge 130 mounted in the head assembly 104 of the illustrated embodiment for indexed rotation on an axis that is parallel to the axis of a shaft 132 leading to the operating tip 108. The shaft 132 mounts on the head assembly in a manner that permits linear translation along its axis. A proximal end 134 of the shaft 132 projects toward a distal side of the cartridge 130. As this particular illustrated embodiment uses a vacuum subsystem, it is shown on the proximal side of the cartridge that a vacuum tube 136 mounts to the head assembly 104 in a manner that permits linear translation of a distal tip thereof.

FIGS. 14A-14D are various views of an exemplary disk-shaped cartridge 130 according to another aspect of the present invention. The cartridge 130 comprises a body 140 defining a plurality of receptacles 142 therein. The body 140 defines an outer cylindrical surface 144, a flat circular distal face (or first face) 146, and a flat circular proximal face (or second face) 148. The axial distance between the faces 146, 148 defines a thickness t dimension, as seen in FIG. 14D. The receptacles 140 extend axially through the body 140 from a first opening 150 at the distal face 146 to a second opening 152 at the proximal face 148. Each of the receptacles 142 is analogous to the receptacles 64 for the previously described cartridge shuttle subsystem 20 of FIGS. 1-9.

FIG. 14A shows the distal side of the cartridge 130 illustrating the distal/first face 146 and the plurality of first openings 150 for the corresponding receptacles 142. The receptacles 142 are arrayed in a circular pattern about the axis of the cartridge 130. In the illustrated embodiment, the circular pattern of receptacles 142 is located close to the periphery of the cartridge (along the circumference), which maximizes the number of receptacles because of a minimum required spacing therebetween. It should be understood that multiple circular or non-circular patterns of receptacles may be provided through the cartridge. As will be described below, the circular pattern of receptacles 142 aligns with the axis of the shaft 132 seen in FIG. 13. Indexing or rotating the cartridge 130, therefore, causes select ones of the receptacles 142 to register with the proximal end 134 of the shaft 132. Of course, the receptacles 142 could be arranged in numerous ways with a corresponding change in the required movement of the cartridge 130 relative to the shaft 132 (or visa versa). For instance, the receptacles 142 could be arranged in a pattern of at least one circular array of receptacles along a circumference of the storage device as shown, or the pattern may include a second (or third, etc.) circular array of receptacles concentrically arranged at a smaller radius than the first one. For that matter, the pattern could be random, or in certain order, have aligned rows or circles, or other arrangements. The pattern is limited only by the potential movement of the cartridge 130 relative to the shaft 132 (or visa versa).

The cartridge 130 further includes a cover 160 on its proximal/second side that extends over the second openings 152 of the receptacles 142. The cover 160 is made of a permissive medium as described below to permit access via a number of means into the receptacle.

The term "permissive medium" refers to any number of materials that could be used with a storage cartridge according to one aspect of the present invention to facilitate movement of a biological unit to or from the cartridge receptacles. Examples of such mediums include meshes, screens, paper, elastomeric materials such as silicone, various contiguous polymers, various resealable materials that allow creation of a slit or puncture that closes or reseals on its own, etc. Any of the above-listed exemplary materials may cover the back (or proximal) side of the cartridge to prevent FUs from passing through and exiting the cartridge, while at the same time allowing air and/or liquids to pass through. The permissive mediums useful in the present invention are used to cover an opening of a receptacle of a cartridge for storing, for example, follicular units (FUs), and must possess sufficient structural integrity to block passage of an FU that is propelled into the receptacle with some velocity. On the other hand, the permissive medium is preferably either porous to permit air or fluid to pass freely therethrough (air/fluid permeable), or is susceptible to puncture with a tool.

One subset of permissive medium is an air and/or fluid permeable medium. If the cover 160 is permeable by air or fluids then a pressure differential through the receptacles can be established across the cover material. For instance, a mesh that permits passage of saline is a permeable medium, and therefore a permissive medium. However, another subset of permissive medium, a "puncturable medium," refers to any number of materials that can relatively easily be punctured or pierced to create an opening, at least temporarily. Note that a "puncturable medium" may be air and/or fluid permeable, as in a mesh, or not. If the cover 160 is fluid impermeable yet puncturable, then for example a pressure differential through the receptacles can be established using a probe that extends into the receptacle through the cover. Even metal may be a puncturable medium if it is very thin, as in a foil, or arranged in a fine mesh or screen. The puncture is accomplished using an obturator (or rod, or needle, typically metallic) so that an opening can be formed to allow for air/fluid passage. The opening may be either permanently formed or temporarily formed in case of resealable medium. Creation of an opening, as mentioned enables introduction of a suction probe for those embodiments and/or steps of the procedure that use pressure differential or vacuum to pull FUs into receptacles of the cartridge. Alternatively, openings may be formed to permit introduction of saline or other known preserving solution to the receptacles.

Examples of puncturable mediums include meshes/screens (e.g., of polymer), medical filter materials that are air-permeable but not fluid permeable, and silicone rubbers. Desirably, the puncturable medium is non-fraying, meaning that the puncture does not result in particles being shed or severed therefrom. Such particles could degrade or contaminate the biological unit in the receptacle.

An exemplary permissive medium may be medical grade silicone rubber poly-dimethylsiloxane (PDMS) which can be punctured by an obturator sized to fit through the receptacles 142. As seen in FIG. 14D, the cover 160 may be attached to the body 140 of the cartridge 130 by virtue of a retaining ring 162. Although not shown, the retaining ring 162 may be fastened to the body 140 with screws or bolts, or glue may be used for a more permanent attachment. Alternatively, the use of the retaining ring is not necessary, and cover 160 could be directly attached (either permanently or removably) to the body of the cartridge, for example by gluing, fusing, clipping, etc. Two different ways for clamping the cover 160 to the body 140 are shown below with respect to FIGS. 17 and 19.

Desirably, an amount of saline or other known preserving solution is placed in each receptacle 142 of the cartridge 130 so that hair follicles or other biological objects remain hydrated or maintain a cool temperature during the storage. One way to accomplish this is to utilize a permissive medium for the cover 160 that wicks the preservative fluid against the second openings 152 and therefore transfers it to each receptacle due to surface tension effects (i.e., capillary action). Another way is to directly insert a drop of fluid into each receptacle 142.

The cartridge 130 (or 30 in the earlier embodiment) is not limited to use with the robotic system of FIG. 10, but also has utility in other procedures. As mentioned, various kinds of biological units may be managed using the cartridge of the present invention. One example is a process where a plurality of biopsy samples are taken and stored for later analysis. The system desirably matches the donor location with the receptacles, and then can deliver any one biopsy sample as needed with knowledge of the area of the body from which it came. Additionally, as mentioned previously, the cartridge may be utilized in a primarily manual system, without the aid of the robotic system described herein. To clarify, the cartridge of the present invention may be utilized in a manual or primarily manual system where harvesting and/or implanting is accomplished by a person (such as, physician or trained technician) using, for example, a hand-held device, even though such device or a procedure may be automated to various degrees.

FIG. 15 is a perspective view of the disk-shaped cartridge 130 prior to loading into a harvesting/implanting system 100. The proximal side of the cartridge is illustrated and it should be noted that the cover 160 is not shown so as to expose the receptacles 142.

FIG. 16 is a perspective view of a cartridge 130 mounted in proximity to certain of the harvesting/implanting system 100 components with which it directly interacts. The cartridge 130 is oriented the same way as in FIG. 15, with the proximal side to the left, though in this operational view the permissive medium cover 160 occludes the receptacles 142. FIG. 16 also illustrates an alternative configuration for mounting the cover 160. With reference also to FIG. 17, inner and outer mounting rings 164a, 164b bolt to the body of the cartridge 130 and hold the retaining rings 166a, 166b within grooves (not numbered) in the proximal face of the cartridge 130. The retaining rings 166a, 166b in turn capture and frictionally hold inner and outer circular edges of the cover 160, which is made of the material that flexes or can be pressed into the grooves. For instance, the cover 160 may be made of a silicone (PDMS) elastomer in the shape of the annulus with the inner and outer edges thereof retained in the grooves by the rings 164, 166.

FIG. 16 shows the vacuum tube 136 passing through a frame member 168 mounted on the head assembly 104 (FIG. 13). A spring member 170 is seen at the terminal end of the vacuum tube 136, which helps ensure good suction contact between the tube and the proximal face of the cartridge 130 and reduces the need for precise relative positioning tolerances. Again, the head assembly 104 includes a movement mechanism (not shown) for translating the vacuum tube 136 toward and away from the cartridge 130, as indicated by the double-headed arrow.

The frame member 168 may also provide a platform for mounting a piercing device 172 adjacent the terminal end of the vacuum tube 136. The piercing device 172 comprises a thin rod, desirably pointed or sharpened, which lies at the same radial distance from the rotational axis of the cartridge 130 as the vacuum tube 136. In other words, the piercing device 172 aligns with the circular pattern of receptacles 142. The piercing device 172 may be utilized to pre-puncture holes or slits through the cover 160 for each of the receptacles. The piercing device 172 may be utilized if the terminal end of the vacuum tube 136 comprises a thin probe for entering the receptacles, and the probe is insufficiently sharp to cleanly form its own hole. Such an embodiment will be described below in reference to FIG. 19. In an alternative configuration, the terminal end of the vacuum tube 136 may be pointed to perform the puncture rather than using a separate piercing instrument.

FIG. 16 also illustrates a housing 174 within which may be located a rotational prime mover, such as a stepper motor, for rotating or indexing the cartridge 130. Precise rotational movement of the cartridge 130 registers each of the receptacles 142 in turn relative to the vacuum tube 136. Software controlling the movement mechanism enables any one of the receptacles 142 to be registered as desired. For example, as mentioned above an inspection system for assessing the characteristic of each FU may be incorporated into the harvesting procedure, and an understanding of what type of FU is in each receptacle 142 enables the system to implant smaller FUs in one location, while larger FUs are implanted in another location. Numerous such implant schemes are known in the art and will not be described further herein. The reader will also note that relative radial translation of the vacuum tube 136 and cartridge 130 may be incorporated into the system to facilitate registration of the vacuum tube 136 with a second circular array of receptacles 142 (not shown) concentrically arranged with respect to the illustrated array.

FIG. 17 is an enlarged sectional view of the distal components of FIG. 16, and illustrates exemplary pressure differential reduction structure desirably provided to slow down the velocity of a biological unit traveling toward the cartridge 130. In one method of use of the system, a source of suction is applied to a proximal side of a selected receptacle 142 during the harvesting process, which creates a pressure differential in the proximal direction thus urging an FU into the receptacle. The magnitude of the pressure differential typically remains constant during travel of the FU along the path from the harvesting tool to the receptacle 142, because the suction required to pull the FU from the body surface is relatively high, which results in the FU moving a high rate of speed toward the receptacle. This high velocity movement potentially may cause damage to the FU when it halts at the proximal end of the cartridge receptacle, such as when it impacts the cover 160. Because of the short travel duration, however, it would be difficult though not impossible to provide a system which steps down the magnitude of the suction halfway between the harvesting tool and the receptacle.

Rather than incorporating a sophisticated (i.e., expensive) dual-stage pressure step-down system, structure may be provided along a path in which the biological unit travels from the removal tool to the storage device receptacle to reduce the pressure differential along a portion thereof and thereby reduce the speed of the FU along the path. For instance, the structure may comprise a parallel flow path outside of the main path which terminates just before the path reaches the cartridge. In FIG. 17, the FU travel path from the operating tip 108 through the distal shaft 132 passes along a main tube 173 surrounded by an outer tube 175. An annular space is created between the tubes 173, 175. Two sets of bypass holes 177 spaced apart substantially the length of the shaft 132 enable flow to enter the annular space. This reduces the pressure within the main tube 173 and therefore slows down travel of the FU in that area.

Figure 18:
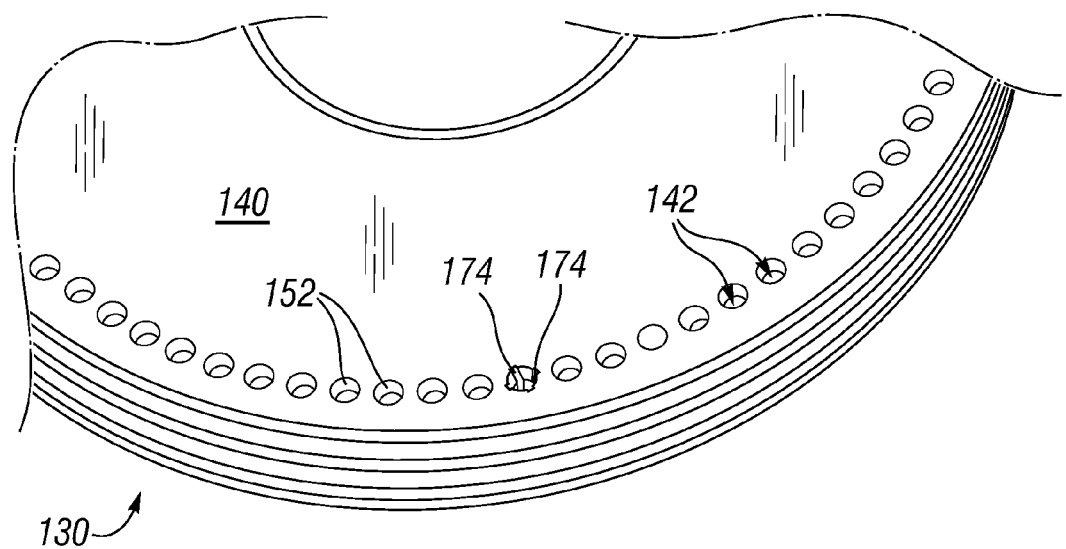
FIG. 18 is a partial perspective view of a proximal side of a cartridge of the present invention showing exemplary pressure relief structure at one of the receptacle openings.

Now with reference to FIG. 18, an exemplary pressure relief structure for the cartridge receptacles 142 is shown. When a source of suction is applied to a proximal side of a selected receptacle 142 during the harvesting process, the pressure differential continues for short period after the FU reaches the receptacle. During that time, it is desirable to mitigate the dehydrating effects of the suction on the FU, for instance if the FU completely includes the receptacle on its proximal side. In FIG. 18, one of the receptacles 142 shown is provided with pressure relief channels 174 to limit the maximum suction created within the receptacle to less than a magnitude of the source of suction. Stated another way, the vacuum tube 136 comprises a source of suction which, if sealed around the proximal end of the receptacle 142, would apply a magnitude of suction to the receptacle. Without the pressure relief channels 174, the FU within the receptacle would be exposed to the maximum suction. By providing alternative paths for fluid or air into the vacuum tube 136, the maximum suction to which the FU is exposed is less than the magnitude of the source of suction.

The pressure relief channels 174 are shown as small notches in a cross pattern at the second opening or proximal end of the receptacle 142. Of course, other configurations can be used, including only one notch. Additionally, the pressure relief channels 174 are only shown in one receptacle for example purposes, and desirably are provided for all the receptacles.

Figure 19:
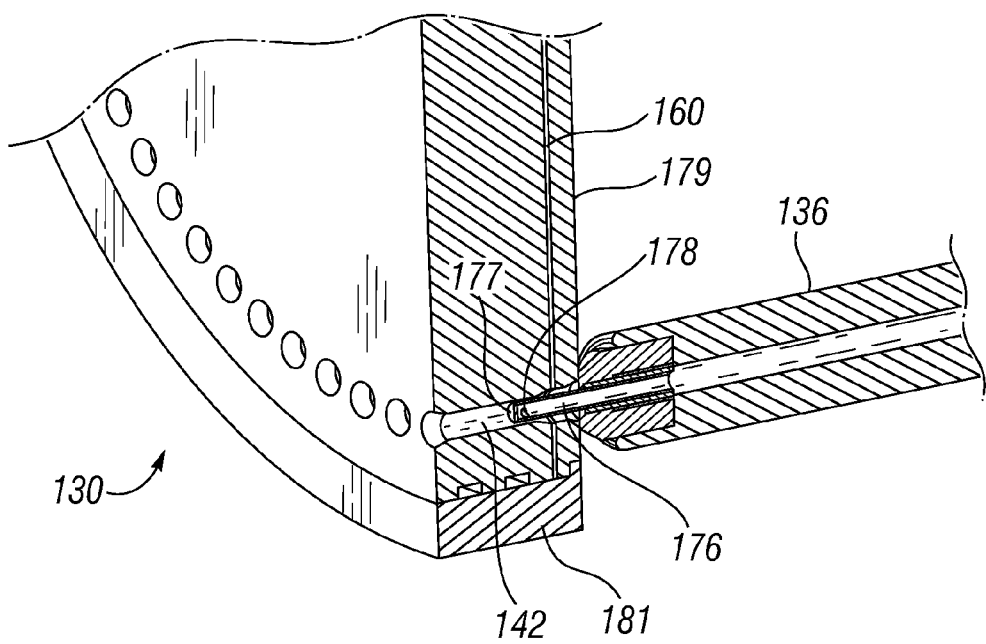
FIG. 19 is a perspective sectional view of one edge of an alternative cartridge of the present invention showing a suction probe extending through a permissive medium into a receptacle.

FIG. 19 illustrates an alternative method for applying a source of suction (creating a pressure differential) to the receptacles 142. Namely, a suction probe 176 extends from the distal end of the vacuum tube 136. The suction probe 176 features a blunt, closed end 177 and at least one side port 178 near the closed end. The outer diameter of the suction probe 176 is sufficiently smaller than the inner diameter of the receptacle 142 so as to provide a gap and permit air or fluid to flow around the probe and into the side port 178.

The suction probe 176 extends through the permissive medium cover 160 into the receptacle 142. In this embodiment, the cover 160 is optionally retained against the proximal face of the cartridge 130 by a plate 179 that is in turn secured by an outer ring 181. A circular array of tapered openings (not numbered) in the plate 179 register with each of the receptacles 142, which facilitates introduction of the probe 176 to the receptacle. Suction probe 176 may be used with any of the permissive mediums, but is especially useful with a cover 160 that is relatively impermissible to fluids. Pulling suction directly through such a material would be impractical, and therefore the probe 176 must be inserted through the cover 160 into the receptacle. Desirably the cover 160 is made of a material that self-seals after removal of the probe 176; for example, silicone (PDMS) elastomer.

The probe 176 may be pushed directly through the cover 160, but given its blunt shape pre-formed slits or holes are desirably provided. For example, the piercing tube 172 illustrated in FIG. 16 may be used to form such holes. A particularly useful piercing tube 172 is shaped in the form of a Huber needle which is designed so as not to core a hole, but instead just form a slit which is self-sealing. Alternatively, the terminal end of the suction probe 176 may be more pointed, such as in the shape of a Huber needle, so as to form the hole itself, but consideration should be given to the effect on the FU when it contacts the sharpened probe.

FIGS. 20 and 21 are perspective and side views isolating follicular unit shuttle components from the overall head assembly 104. These components can also be seen incorporated in head assembly 104 in FIGS. 11-13. To describe important operational interactions of the system, or relative movement between the distal end of the system including operating tip 108, the cartridge 130, and the proximal end of the system including vacuum tube 136 will be described. FIGS. 22A-22D illustrate a sequence for harvesting an FU, while FIGS. 23A-23B describe a sequence for implanting an FU. It should be understood that these operations may be carried out sequentially by first filling the cartridge 130, and then emptying it without detaching from the system. However, depending on the number of receptacles 142 in the cartridge 130, several cartridges may be required and the harvesting operation is accomplished first before the implant procedure. For instance, a cartridge may hold 125-500 FUs, while a typical procedure requires up to 2000 FUs. The number of receptacles is of course variable and a single cartridge may hold all that would be needed.

Figure 22C:
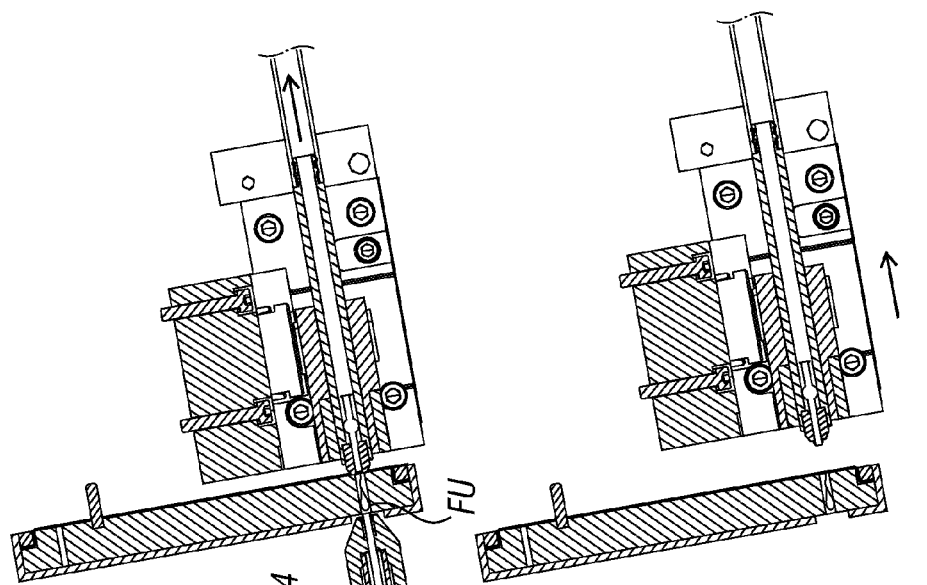

FIGS. 22A-22D are sectional views through the shuttle components taken along line 22-22 of FIG. 20, showing a sequence of operation for harvesting or removing a follicular unit from a body surface 110 and shuttling it to the cartridge 130. In FIG. 22A, the shaft 132 is shown after having been displaced to the left within a cylinder 180. This action causes a harvesting/removal tool 182 to punch into the body surface 110 to a predetermined depth. The depth of penetration of the tool 182 is determined with knowledge of the distance between the tool and the body surface prior to displacement of the shaft 132.

In FIG. 22B, a follicular unit FU is shown positioned within a lumen of the removal tool 182. Also, the assembly of the shaft 132 and cylinder 180 is shown translated to the right so that the proximal end 134 contacts the cartridge 130. The throughbore of the shaft 132 registers with one of the receptacles 142 in the cartridge 130.

FIG. 22C illustrates a step wherein the FU shuttles from the removal tool 182 through the shaft 132 and into the cartridge receptacle 142. This may be accomplished using a pressure differential created, for example, by suction through the vacuum tube 136. This step of shuttling the FU in FIG. 22C desirably utilizes the velocity reducing bypass structure described above with respect to FIG. 17, as well as the pressure reduction channels described with respect to FIG. 18. Alternatively, a mechanical shuttle may be utilized to transfer the FU into the receptacle 142. For instance, a rod or obturator (not shown) may be provided that extends through the shaft 132 and pushes the FU until it deposits into the receptacle 142.

Figure 22D:
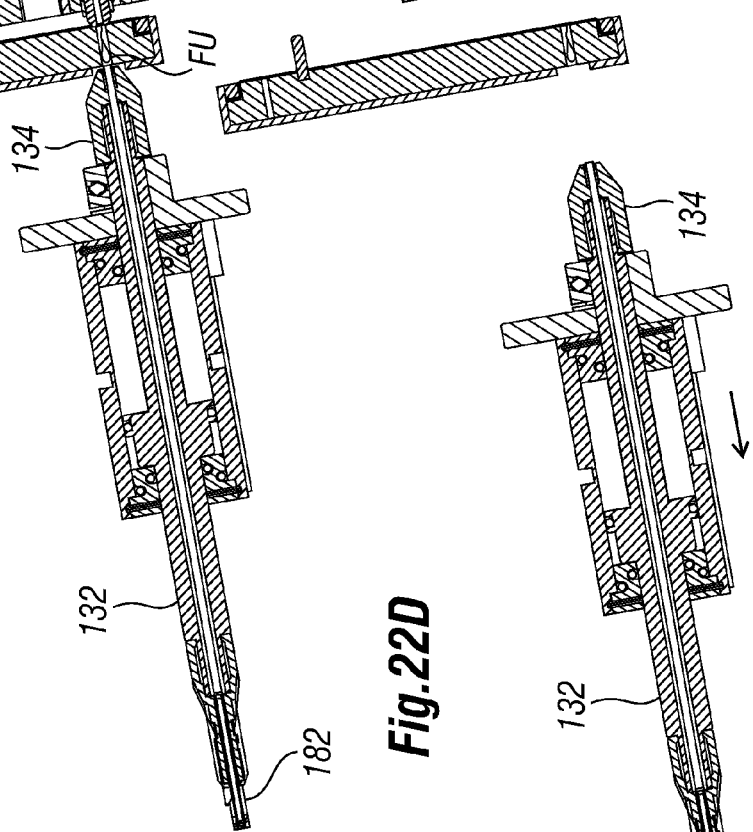

Finally, FIG. 22D shows the assembly including the shaft 132 moving away from the cartridge 130 into distal direction, and the assembly including the vacuum tube 136 moving away from the cartridge 130. At this point, the cartridge 130 is free to rotate and index another receptacle into registration with the distal and proximal components of the shuttle subsystem.

Now with reference to FIG. 23A, the shuttle subsystem components are shown essentially in the positions from FIG. 22D, although instead of a harvesting/removal tool, the distal end of the shaft 132 features an implant tool 184. A receptacle 142 having an FU registers with the lumen of the shaft 132. On the proximal side, the vacuum tube 136 has been removed and replaced with a solid rod-like obturator 186. The obturator 186 translates linearly along its axis through the receptacle 142 and through the entire length of the shaft 132, and may be propelled in a number of ways including by contact with a plurality of wheels 188.

FIG. 23B shows the three components brought together and the obturator 186 passed though the receptacle 142 and entire shaft 132 until the FU reaches the implant tool 184. The implant tool 184 may be used to deposit the FU into a preformed incision or create a new incision in a body surface.

The reader should understand that shuttling of the hair follicles from the cartridge to the implant tool could be accomplished using several alternative approaches. One example is to push the FUs from the cartridge all the way through the distal end of the implant tool using the obturator as described. Another option is to use a pressure differential to urge the FU out of each receptacle and into the implant tool. For example, the vacuum tube 136 described above that creates a pressure differential urging the FU in the proximal direction can also be used to reverse the pressure differential to propel the FU distally. Or, a combination of physical pushing and pressure could be used.

The foregoing illustrated and described embodiments of the invention are susceptible to various modifications and alternative forms, and it should be understood that the invention generally, as well as the specific embodiments described herein, are not limited to the particular forms or methods disclosed, and that many other embodiments are possible within the spirit and the scope of the present invention. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

While the invention has been described in its preferred embodiments, it is to be understood that the words which have been used are words of description and not of limitation. Therefore, changes may be made within the appended claims without departing from the true scope of the invention.

What is claimed is:

1. A device for transplanting biological units into tissue, comprising:
    a robotic system having a robotic arm and one or more control mechanisms;
    an implanting tool having a lumen therethrough, the implanting tool being connected to and manipulated by the robotic arm; and
    a cartridge having a plurality of receptacles each sized and configured to retain a biological unit,
    wherein the one or more control mechanisms is configured to automatically align the selected cartridge receptacle with the lumen of the implanting tool and urge the biological unit from the selected receptacle through the lumen of the implanting tool into the tissue.

2. The device of claim 1, wherein the cartridge is substantially cylindrical or disk-shaped and the plurality of receptacles are arrayed in a pattern.

3. The device of claim 1, wherein the cartridge is substantially linear or rectilinear.

4. The device of claim 1, further comprising an obturator positioned to pass through the selected cartridge receptacle, and wherein the control mechanism directs passage of the obturator through the selected cartridge receptacle to urge the biological unit from the selected cartridge receptacle.

5. The device of claim 1, further comprising a pressure differential through the selected cartridge receptacle, and wherein the control mechanism initiates the pressure differential through the selected cartridge receptacle to urge the biological unit from the selected cartridge receptacle.

6. The device of claim 1, wherein the biological unit is a hair graft, and the receptacles are sized to closely receive the hair graft.

7. The device of claim 1, wherein the biological unit is a skin unit or tissue for grafting.

8. The device of claim 1, wherein at least one of the plurality of receptacles comprises a pressure relief structure that limits the maximum suction created within the receptacle from a source of suction.

9. The device of claim 8, wherein the pressure relief structure comprises one or more notches.

10. The device of claim 1, wherein the cartridge is disposable.

11. The device of claim 1, wherein the cartridge comprises a permissive medium and is configured to be removably received in a robotic system.

12. The device of claim 1, wherein at least one receptacle of the plurality of receptacles contains a biological unit preservation solution.

13. The device of claim 1, wherein at least one of the plurality of receptacles has a tapered opening.

14. A method of implanting a biological unit using a cartridge having a plurality of receptacles, the method comprising:
    urging the biological unit into a selected receptacle of the cartridge and capturing the biological unit in the selected cartridge receptacle;
    displacing the biological unit from the selected cartridge receptacle into a lumen of an implanting tool, using a substantially automated process; and
    urging the biological unit from the lumen of the implanting tool into a recipient area using a substantially automated process.

15. The method of claim 14, wherein the step of urging the biological unit from the lumen of the implanting tool comprises pushing the biological unit through the lumen of the implanting tool using mechanical means.

16. The method of claim 14, further comprising cooling the biological unit while it is stored in a cartridge receptacle.

17. The method of claim 14, further comprising preserving the biological unit while it is stored in the receptacle of the cartridge with a preservation solution.

18. The method of claim 14, comprising loading the biological unit into one of the plurality of receptacles of the cartridge.

19. The method of claim 14, wherein the implanting tool is coupled to a robotic arm, and at least some of the steps of the process are performed utilizing the robotic arm.

20. The method of claim 14, wherein the biological unit is a hair follicular unit, a tissue graft, or a skin graft.

* * * * *